(12) United States Patent
Oikawa et al.

(10) Patent No.: US 7,291,747 B2
(45) Date of Patent: Nov. 6, 2007

(54) SILICON COMPOUNDS AND PROCESS FOR PREPARATION THEREOF

(75) Inventors: Hisao Oikawa, Yokohama (JP);
Kenichi Watanabe, Yokohama (JP);
Nobumasa Ootake, Yokohama (JP);
Kazuhiro Yoshida, Yokohama (JP);
Keizou Iwatani, Yokohama (JP)

(73) Assignee: Chisso Corporation, Osaka (JP)

( * ) Notice: Subject to any disclaimer, the term of this patent is extended or adjusted under 35 U.S.C. 154(b) by 446 days.

(21) Appl. No.: 10/478,483

(22) PCT Filed: May 17, 2002

(86) PCT No.: PCT/JP02/04776

§ 371 (c)(1),
(2), (4) Date: Nov. 21, 2003

(87) PCT Pub. No.: WO02/094839

PCT Pub. Date: Nov. 28, 2002

(65) Prior Publication Data

US 2004/0143081 A1 Jul. 22, 2004

(30) Foreign Application Priority Data

May 21, 2001 (JP) .............................. 2001-150408
Jun. 28, 2001 (JP) .............................. 2001-196154

(51) Int. Cl.
*C07F 7/00* (2006.01)
(52) U.S. Cl. ..................................................... 556/443
(58) Field of Classification Search ................. 556/460
See application file for complete search history.

(56) References Cited

FOREIGN PATENT DOCUMENTS

WO   WO 01/10871   2/2001

OTHER PUBLICATIONS

Annand et al (Inorg. Chem. vol. 38, pp. 3941-3943, 1999).*
Frank J. Feher et al., "Facile Synthesis of New Incompletely Condensed Polyhedral Oligosilsesquioxanes", Organometallics, vol. 10, No. 7, pp. 2526-2528, 1991.
Frank J. Feher et al., "A new route to incompletely-condensed silsesquioxanes: base-mediated cleavage of polyhedral oligosilsesquioxanes", Chemical Communications, No. 22, pp. 2309-2310, 1999.
J. A. Tossell, "Theoretical Studies of Si and Al Distributions in Molecules and Minerals with Eight Tetrahedrally Coordinated Atoms ($T_8$) in Double Four-Ring (D4R) Geometries: Octasilasesquioxanes, Gismondite, and Zeolite A", Journal of Physical Chemistry, vol. 100, No. 35, pp. 14828-14834, 1996.
Vincent Ruffieux, "$T_8$-OSS-Ethyldiphenylphosphine: A New Functional Oligosilsesquioxane Ligand", Chem. Eur. J., 3, No. 6, pp. 900-903, 1997.

* cited by examiner

*Primary Examiner*—Samuel Barts
(74) *Attorney, Agent, or Firm*—Wenderoth, Lind & Ponack, L.L.P.

(57) ABSTRACT

An organic silicon compound, having high reactivity, represented by the following Formula (1):

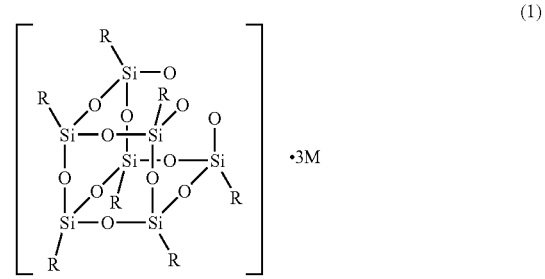

wherein R and M are defined in the specification. The organic silicon compound is produced by reacting polysilsesquioxane, which is obtained by hydrolyzing a silane compound having three hydrolyzable groups and represented by the following Formula (2), with a monovalent alkaline metal hydroxide in an organic solvent, or by subjecting the silane compound having three hydrolyzable groups to hydrolysis and polycondensation in the presence of an organic solvent and an alkaline metal hydroxide:

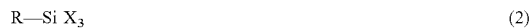

wherein R is the same as in Formula (1) and X represents a hydrolyzable group.

38 Claims, 7 Drawing Sheets

Number average molecular weight  Mn:                     682
Weight average molecular weight  Mw:                     686
Z average molecular weight  Mz:           -              690
Viscosity average molecular weight  Mv:                  686
Polydispersity Index  Mw/Mn:    1.0055    Mz/Mw    1.0056

SILICON COMPOUNDS AND PROCESS FOR PREPARATION THEREOF

FIELD OF THE INVENTION

The present invention relates to a novel organic silicon compound in which a structure is prescribed. More specifically, it relates to a novel organic silicon compound which has a reaction active group and from which capable of being derived are various organic silicon compounds useful for a modifying agent for thermoplastic resins, an interlayer dielectric, a sealing material, a coating material and a flame retardant making use of this reaction active group, and a production process for the same.

BACKGROUND OF THE INVENTION

An organic silicon compound intermediate having a structure represented by the following Formula (3) has so far been known as an intermediate from which various organic silicon compounds useful for a modifying agent for thermoplastic resins can be derived:

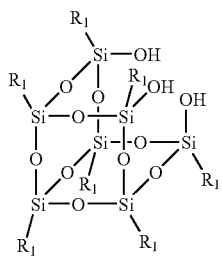

(3)

$R_1$ in Formula (3) is hydrogen, methyl, isobutyl, cyclohexyl, cyclopentyl, phenyl or vinylhexyl. And these $R_1$'s are the same group.

Such compound is usually synthesized by hydrolyzing chlorosilane and ripening. Frank J. Feher et al. of California University obtained the compound represented by Formula (3) described above by reacting cyclopentyltrichlorosilane in a mixed solvent of water and acetone at a room temperature or a refluxing temperature and ripening it for further 2 weeks (Organometallics, 10, p. 2526 to 2528 (1991) and Chemical European Journal (Chem. Eur. J.), 3, No. 6, p. 900 to 903 (1997)).

New organic silicon compounds can be derived from such publicly known organic silicon compound by making use of a reactivity of silanol (Si—OH), and when industrially synthesizing derivatives, desired are compounds having an active group which has a higher reactivity than that of the above silanol and which produces less by-products.

When industrially making use of them, desired is a reaction in which synthesis of such publicly known organic silicon compounds is completed for short time and in which by-products are less likely to be produced and a yield is high. However, the publicly known production process described above, have the problems that long time is required for the synthesis and that a lot of by-products are produced and a yield of the target compounds is low.

Further, when the derivatives of new organic silicon compounds are synthesized from such publicly known organic silicon compounds and chlorosilanes, hydrogen chloride is produced by reacting hydrogen of silanol with chlorine of chlorosilane, but hydrogen chloride is not produced by using the organic silicon compound of the present invention even if it is reacted with chlorosilanes, and therefore the reaction can more readily be handled from an industrial point of view.

DISCLOSURE OF THE INVENTION

The present inventors have repeated intensive researches of an intermediate which has a high reactivity and from which obtained is an organic silicon compound useful as a modifying agent for thermoplastic resins, an interlayer dielectric, a sealing material, a coating material and a flame retardant. As a result thereof, they have found that a novel organic silicon compound represented by the following Formula (1) can be produced at a high yield for short time by reacting polysilsesquioxane, which is obtained by hydrolyzing a silane compound having three hydrolyzable groups, with a monovalent alkaline metal hydroxide in an organic solvent, or by subjecting a silane compound having three hydrolyzable groups to hydrolysis and polycondensation in the presence of an organic solvent and an alkaline metal hydroxide. Also, they have found that the compound represented by the above Formula (1) shows a higher reactivity than that of a silanol group of a compound represented by Formula (3), and that the derivative can easily be synthesized at a good yield. Further, they have found that introduction of ONa in place of conventional OH makes it possible to readily handle the reaction without producing hydrogen chloride in a synthetic reaction of the derivative of the above organic silicon compound using chlorosilanes, and that a complete condensation product can be derived by reacting with trichlorosilanes. The present invention has been completed based on these knowledges.

The compound represented by Formula (1) according to the present invention can not be synthesized by the methods disclosed in Organometallics, 10, p. 2526 to 2528 (1991) and Chemical European Journal (Chem. Eur. J.), 3, No. 6, p. 900 to 903 (1997). Further, a method for deriving the compound represented by Formula (1) according to the present invention from the compound represented by Formula (3) has not yet been known.

As apparent from the above descriptions, an object of the present invention is to provide a novel organic silicon compound which has a high reactivity and from which capable of being derived is a novel organic silicon compound useful as a modifying agent for thermoplastic resins, an interlayer dielectric, a sealing material, a coating material and a flame retardant, and a process for producing the same at a good yield.

The present invention is shown by the followings.

(1) An organic silicon compound represented by the following Formula (1):

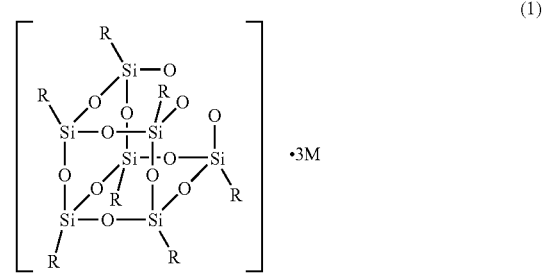

(1)

wherein R represents independently a hydrogen atom, a linear or branched alkyl group, a partially or wholly cyclic alkyl group, a linear or branched alkenyl group, a partially or wholly cyclic alkenyl group, a substituted or non-substituted aryl group, a substituted or non-substituted arylalkyl group, or a substituted or non-substituted arylalkenyl group; at least one hydrogen atom contained in the alkyl group and alkenyl group may be replaced by a fluorine atom, and at least one —$CH_2$—, which is not adjacent, may be replaced by —O—; at least one hydrogen atom in alkylene contained in the arylalkyl group may be replaced by a fluorine atom, and at least one —$CH_2$—, which is not adjacent, may be replaced by —O—; at least one hydrogen atom in alkenylene contained in the arylalkenyl group may be replaced by a fluorine atom, and at least one —$CH_2$—, which is not adjacent, may be replaced by —O—; these selected R's may be the same or different; and M represents a monovalent alkaline metal.

(2) The organic silicon compound as described in the item (1), wherein R in Formula (1) represents independently a hydrogen atom, a linear or branched alkyl group having 44 or less carbon atoms, a partially or wholly cyclic alkyl group having 44 or less carbon atoms, a linear or branched alkenyl group having 45 or less carbon atoms, a partially or wholly cyclic alkenyl group having 45 or less carbon atoms, a substituted or non-substituted aryl group, a substituted or non-substituted arylalkyl group, or a substituted or non-substituted arylalkenyl group; at least one hydrogen atom contained in the alkyl group and alkenyl group may be replaced by a fluorine atom, and at least one —$CH_2$—, which is not adjacent, may be replaced by —O—; in alkylene contained in the arylalkyl group, at least one hydrogen atom may be replaced by a fluorine atom, and at least one —$CH_2$—, which is not adjacent, may be replaced by —O—; in alkenylene contained in the above arylalkenyl group, at least one hydrogen atom may be replaced by a fluorine atom, and at least one —$CH_2$—, which is not adjacent, may be replaced by —O—; and these selected R's may be the same or different.

(3) The organic silicon compound as described in the item (1), wherein R in Formula (1) represents independently a hydrogen atom, a linear or branched alkyl group having 30 or less carbon atoms, or a partially or wholly cyclic alkyl group having 30 or less carbon atoms; at least one hydrogen atom contained in the alkyl group may be replaced by a fluorine atom, and at least one —$CH_2$—, which is not adjacent, contained in the alkyl group may be replaced by —O—; and these selected R's may be the same or different.

(4) The organic silicon compound as described in the item (1), wherein R in Formula (1) represents independently a linear alkenyl group having 22 or less carbon atoms, or a partially or wholly cyclic alkenyl group having 22 or less carbon atoms; at least one —$CH_2$—, which is not adjacent, contained in the alkenyl group may be replaced by —O—; and these selected R's may be the same or different.

(5) The organic silicon compound as described in the item (1), wherein R in Formula (1) represents independently a naphthalenyl group or a phenyl group; at least one hydrogen atom contained in the phenyl group may be replaced by a fluorine atom, a chlorine atom, a bromine atom, a linear or branched alkyl group having 10 or less carbon atoms, a linear or branched alkenyl group having 4 or less carbon atoms (at least one hydrogen atom contained in the alkenyl group may be replaced by a phenyl group), a linear or branched alkoxy group having 18 or less carbon atoms, a phenoxy group, a phenyl group or a phenylmethyl group, and the substituents selected may be the same or different, but when different, they may be any combination of a methyl group and a fluorine atom, a methyl group and a chlorine atom, a methyl group and a bromine atom, an ethenyl group and a fluorine atom, an alkoxy group and a fluorine atom, an alkoxy group and a chlorine atom, and an alkoxy group and a bromine atom; and these selected R's may be the same or different.

(6) The organic silicon compound as described in the item (1), wherein R in Formula (1) represents independently a linear or branched phenylalkyl group having 17 or less carbon atoms, or a partially or wholly cyclic phenylalkyl group having 17 or less carbon atoms; at least one hydrogen atom in a phenyl group contained in the phenylalkyl group may be replaced by a fluorine atom, a chlorine atom, a bromine atom, a linear, branched, or partially or wholly cyclic alkyl group having 12 or less carbon atoms (at least one hydrogen atom contained in the alkyl group may be replaced by a fluorine atom), a linear alkenyl group having 3 or less carbon atoms, a linear alkoxy group having 10 or less carbon atoms (at least one hydrogen atom contained in the alkoxy group may be replaced by a fluorine atom), a methoxymethyl group, a phenoxy group or a phenyl group, and the substituents selected may be the same or different, but when different, they may be any combination of a methyl group and a methoxy group, a methyl group and a chlorine atom, a methyl group and a bromine atom, and a methoxy group and a chlorine atom; at least one —$CH_2$—, which is not adjacent, in alkylene contained in the phenylalkyl group may be replaced by —O—; and these selected R's may be the same or different.

(7) The organic silicon compound as described in the item (1), wherein R in Formula (1) represents independently a linear or branched phenylalkenyl group having 20 or less carbon atoms; at least one hydrogen atom in a phenyl group contained in the phenylalkenyl group may be replaced by a fluorine atom or a methyl group; and these selected R's may be the same or different.

(8) The organic silicon compound as described in the item (1), wherein R in Formula (1) represents independently a linear, branched, or partially or wholly cyclic alkyl group having 8 or less carbon atoms (in the alkyl group, at least one hydrogen atom may be replaced by a fluorine atom, and at least one —$CH_2$—, which is not adjacent, may be replaced by —O—), a linear alkenyl group having 9 or less carbon atoms, a partially or wholly cyclic alkenyl group having 9 or less carbon atoms, a phenyl group, a non-substituted naphthalenyl group, or a linear or branched phenylalkyl group having 10 or less carbon atoms; at least one hydrogen atom contained in the phenyl group may be replaced by a fluorine atom, a chlorine atom, a bromine atom, a methyl group or a methoxy group; at least one hydrogen atom in a phenyl group contained in the phenylalkyl group may be replaced by a fluorine atom, a linear or branched alkyl group having 4 or less carbon atoms, an ethenyl group or a methoxy group; one —$CH_2$— in alkylene contained in the phenylalkyl group may be replaced by —O—; and these selected R's may be the same or different.

(9) The organic silicon compound as described in the item (1), wherein R in Formula (1) represents a linear, branched, or partially or wholly cyclic alkyl group having 8 or less carbon atoms (in the alkyl group, at least one hydrogen atom may be replaced by a fluorine atom, and at least one —$CH_2$—, which is not adjacent, may be replaced by —O—), a linear alkenyl group having 9 or less carbon atoms, a partially or wholly cyclic alkenyl group having 9 or less carbon atoms, a phenyl group, a non-substituted naphthalenyl group, or a linear or branched phenylalkyl group having 10 or less carbon atoms; at least one hydrogen atom contained in the phenyl group may be replaced by a fluorine atom, a chlorine atom, a bromine atom, a methyl group or a methoxy group; at least one hydrogen atom in a phenyl group contained in the phenylalkyl group may be replaced by a fluorine atom, a linear or branched alkyl group having 4 or less carbon atoms, an ethenyl group or a methoxy group; one —CH$_2$— in alkylene contained in the phenylalkyl group may be replaced by —O—; and these selected R's are the same.

(10) The organic silicon compound as described in the item (1), wherein R in Formula (1) represents a phenyl group (at least one hydrogen atom contained in the phenyl group may be replaced by a fluorine atom, a chlorine atom, a bromine atom, a methyl group or a methoxy group), a non-substituted naphthalenyl group, or a linear or branched phenylalkyl group having 10 or less carbon atoms; at least one hydrogen atom in a phenyl group contained in the phenylalkyl group may be replaced by a fluorine atom, a linear or branched alkyl group having 4 or less carbon atoms, an ethenyl group or a methoxy group; one —CH$_2$— in alkylene contained in the phenylalkyl group may be replaced by —O—; and these selected R's are the same group.

(11) The organic silicon compound as described in the item (1), wherein R in Formula (1) is a non-substituted phenyl group.

(12) The organic silicon compound as described in the item (1), wherein the monovalent alkaline metal represented by M is sodium.

(13) A production process for the organic silicon compound represented by Formula (1) as described in the item (1), characterized by reacting polysilsesquioxane, which is obtained by hydrolyzing a silane compound having three hydrolyzable groups and represented by the following Formula (2), with a monovalent alkaline metal hydroxide in an organic solvent:

(2)

wherein R is the same as R described in the item (1), and X represents a hydrolyzable group.

(14) The production process for the organic silicon compound as described in the item (13), wherein R in Formula (2) is the same as R described in the item (2).

(15) The production process for the organic silicon compound as described in the item (13), wherein R in Formula (2) is the same as R described in the item (3).

(16) The production process for the organic silicon compound as described in the item (13), wherein R in Formula (2) is the same as R described in the item (4).

(17) The production process for the organic silicon compound as described in the item (13), wherein R in Formula (2) is the same as R described in the item (5).

(18) The production process for the organic silicon compound as described in the item (13), wherein R in Formula (2) is the same as R described in the item (6).

(19) The production process for the organic silicon compound as described in the item (13), wherein R in Formula (2) is the same as R described in the item (7).

(20) The production process for the organic silicon compound as described in the item (13), wherein R in Formula (2) is the same as R described in the item (8).

(21) The production process for the organic silicon compound as described in the item (13), wherein R in Formula (2) is the same as R described in the item (9).

(22) The production process for the organic silicon compound as described in the item (13), wherein R in Formula (2) is the same as R described in the item (10).

(23) The production process for the organic silicon compound as described in the item (13), wherein R in Formula (2) is the same as R described in the item (11).

(24) A production process for the organic silicon compound represented by Formula (1) as described in the item (1), characterized by subjecting the silane compound, having three hydrolyzable groups and represented by Formula (2) as described in the item (13), to hydrolysis and polycondensation in the presence of an organic solvent and an alkaline metal hydroxide.

(25) The production process for the organic silicon compound as described in the item (24), wherein R in Formula (2) is the same as R described in the item (2).

(26) The production process for the organic silicon compound as described in the item (24), wherein R in Formula (2) is the same as R described in the item (3).

(27) The production process for the organic silicon compound as described in the item (24), wherein R in Formula (2) is the same as R described in the item (4).

(28) The production process for the organic silicon compound as described in the item (24), wherein R in Formula (2) is the same as R described in the item (5).

(29) The production process for the organic silicon compound as described in the item (24), wherein R in Formula (2) is the same as R described in the item (6).

(30) The production process for the organic silicon compound as described in the item (24), wherein R in Formula (2) is the same as R described in the item (7).

(31) The production process for the organic silicon compound as described in the item (24), wherein R in Formula (2) is the same as R described in the item (8).

(32) The production process for the organic silicon compound as described in the item (24), wherein R in Formula (2) is the same as R described in the item (9).

(33) The production process for the organic silicon compound as described in the item (24), wherein R in Formula (2) is the same as R described in the item (10).

(34) The production process for the organic silicon compound as described in the item (24), wherein R in Formula (2) is the same as R described in the item (11).

(35) The production process for the organic silicon compound as described in the item (13) or (24), wherein metal of the monovalent alkaline metal oxide is sodium.

(36) The production process for the organic silicon compound as described in the item (13) or (24), wherein the organic solvent is alcohol or ether.

DETAILED DESCRIPTION OF THE INVENTION

Figure 1:
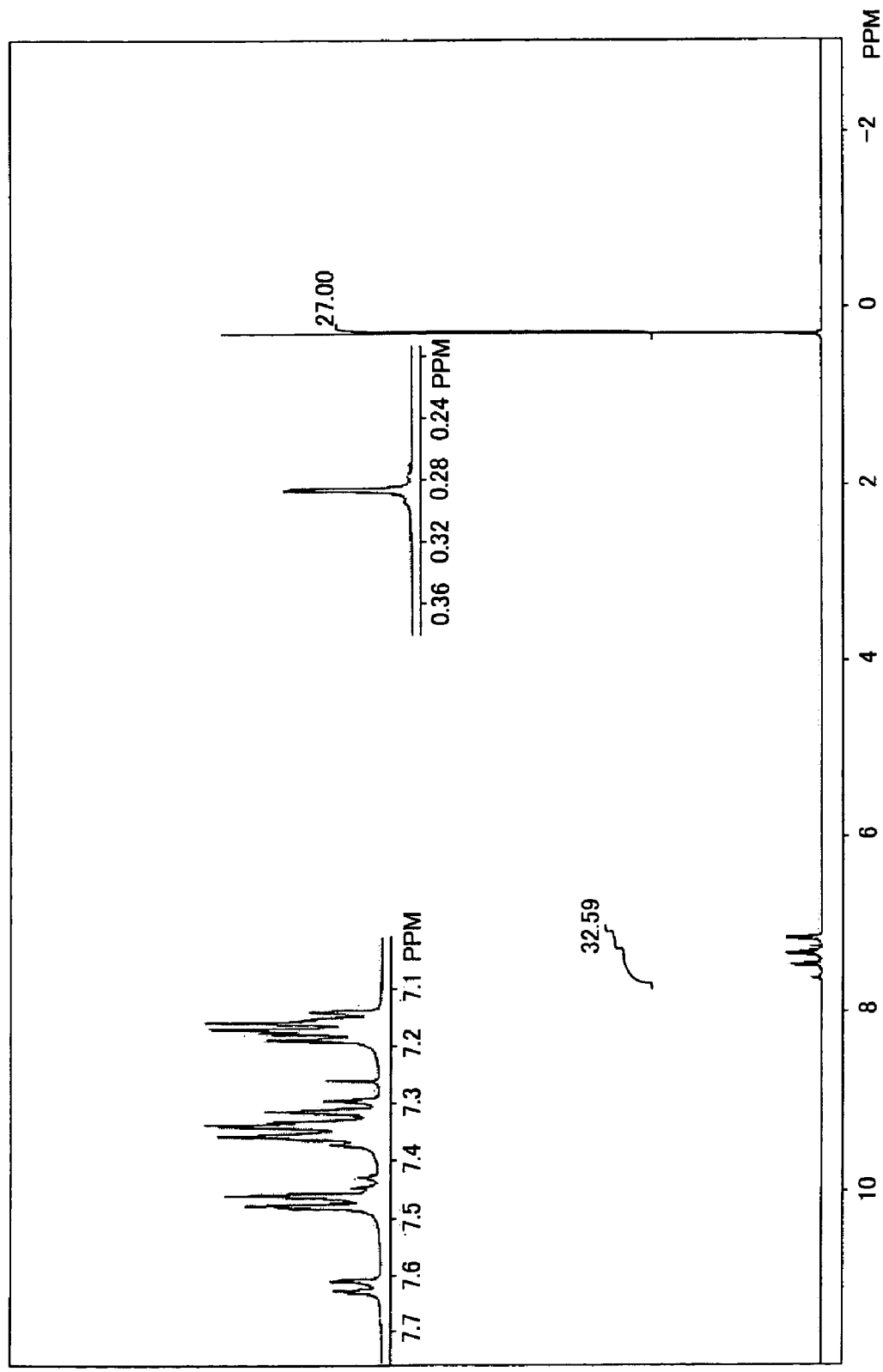
FIG. 1 is a $^1$H-NMR chart diagram of the organic silicon compound synthesized in Example 4.
Figure 2:
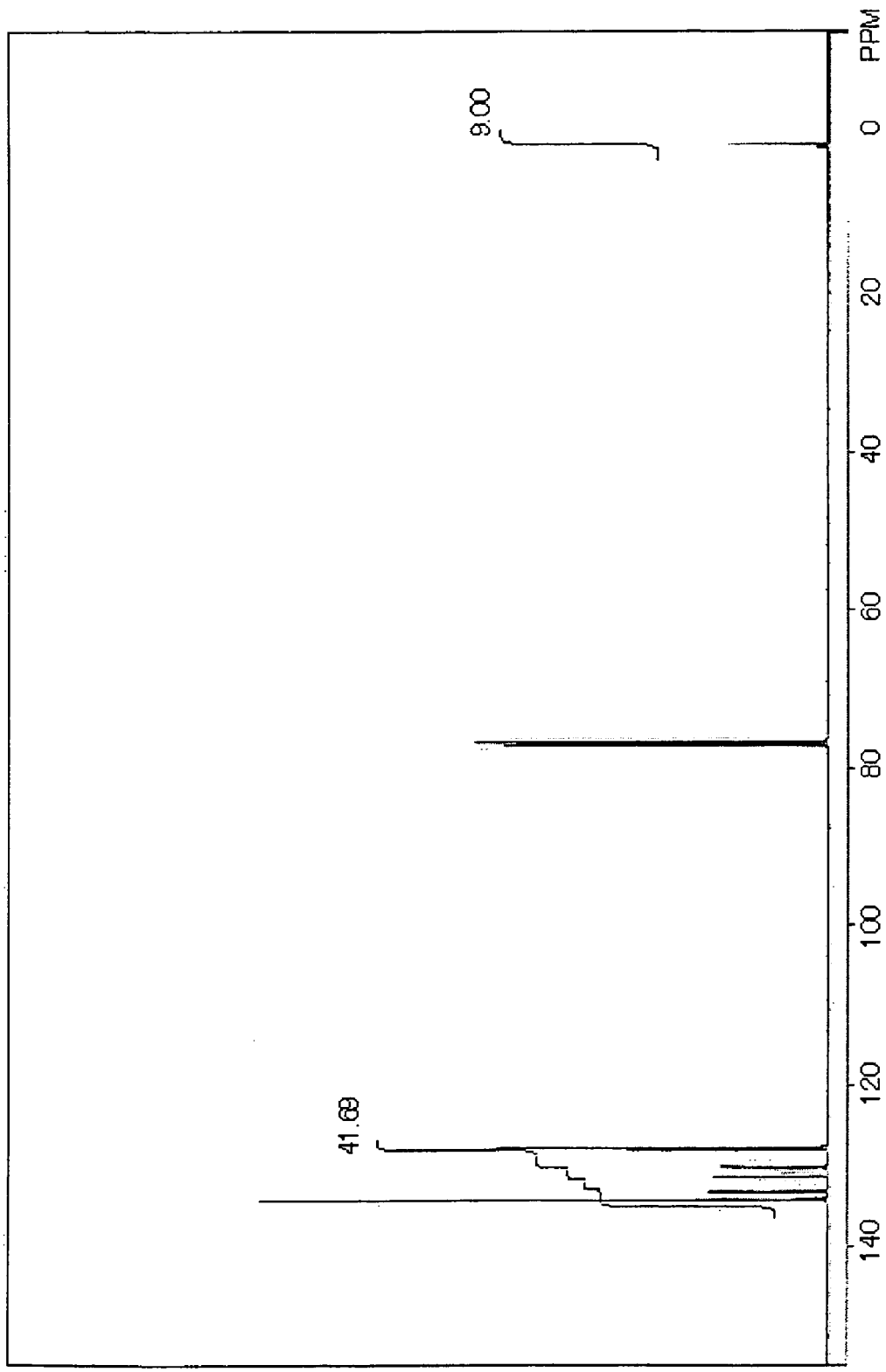
FIG. 2 is a $^{13}$C-NMR chart diagram of the organic silicon compound synthesized in Example 4.
Figure 3:
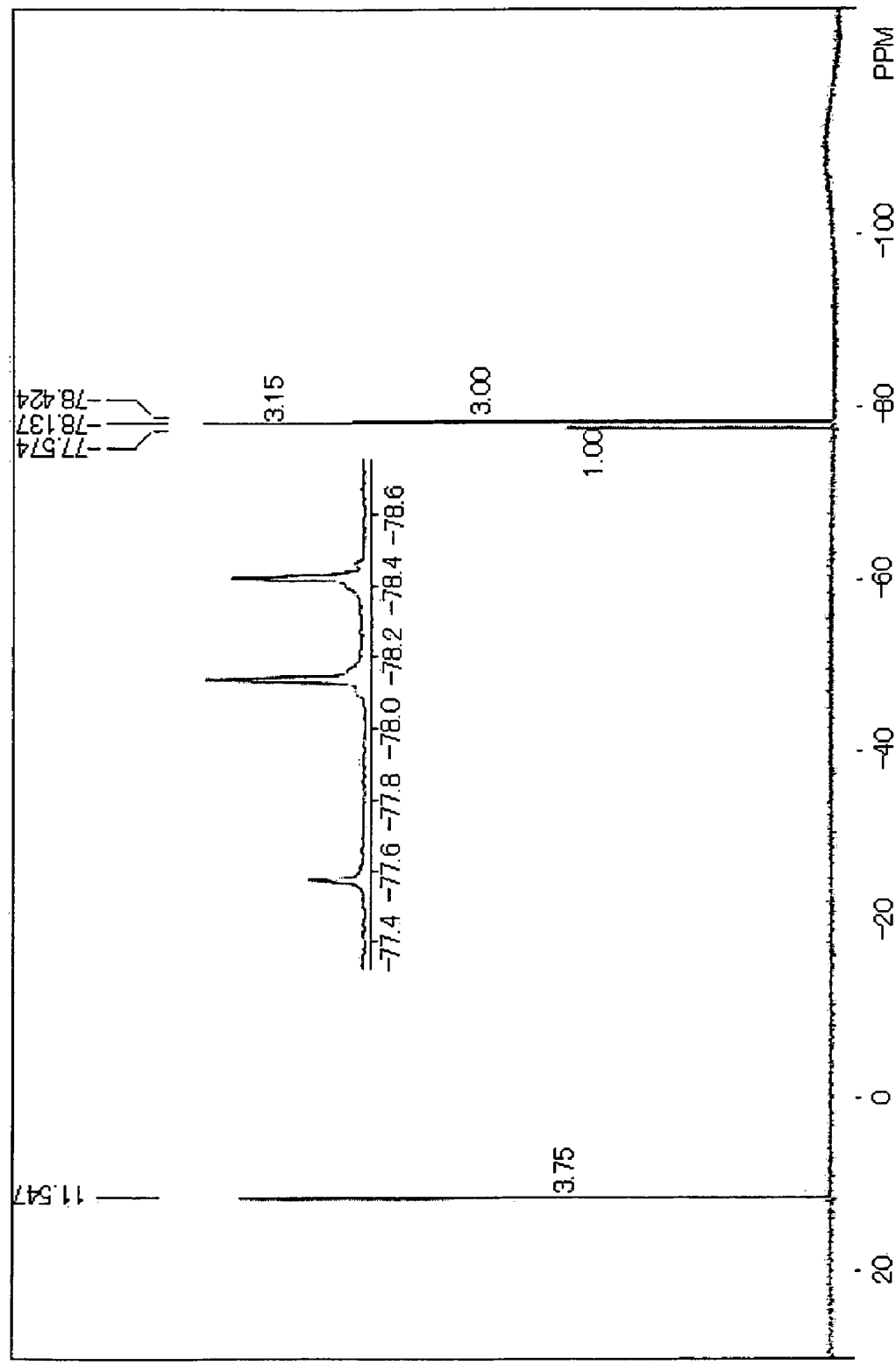
FIG. 3 is a $^{29}$Si-NMR chart diagram of the organic silicon compound synthesized in Example 4.
Figure 4:
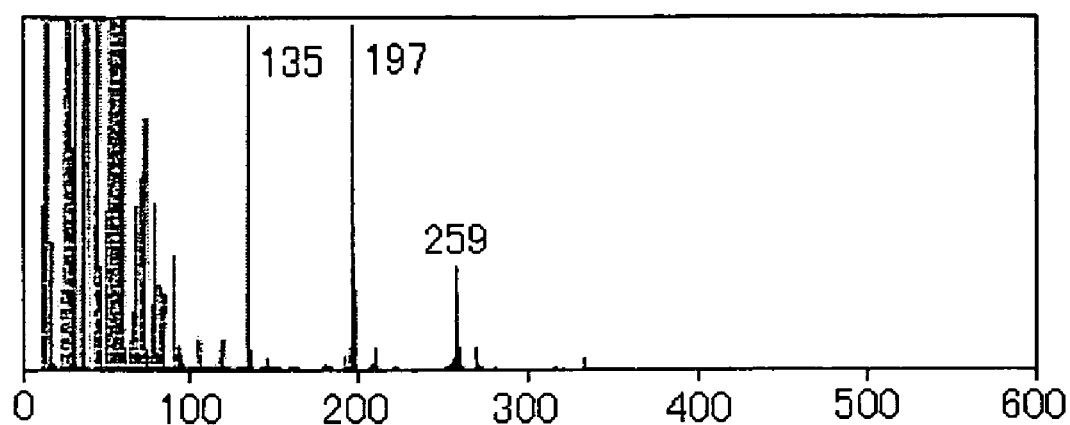
FIG. 4 is a mass spectrometric spectrum diagram of the organic silicon compound synthesized in Example 4.
Figure 4:
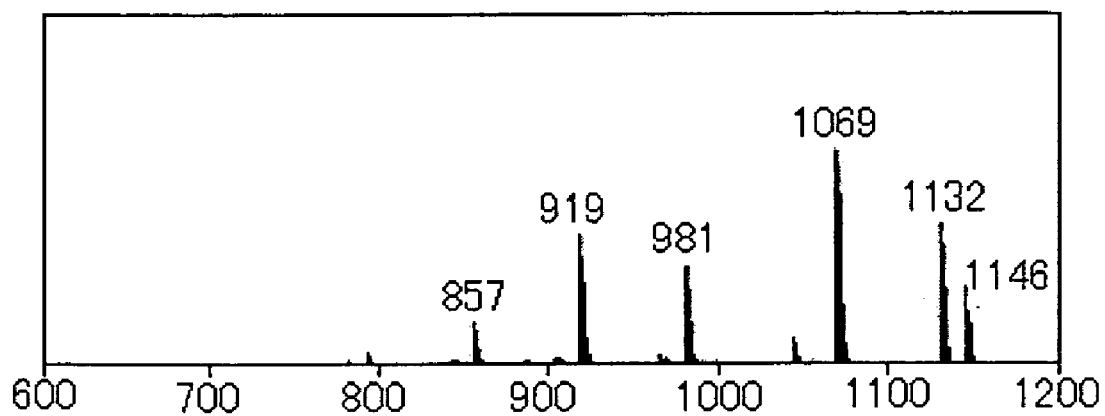
Figure 5:
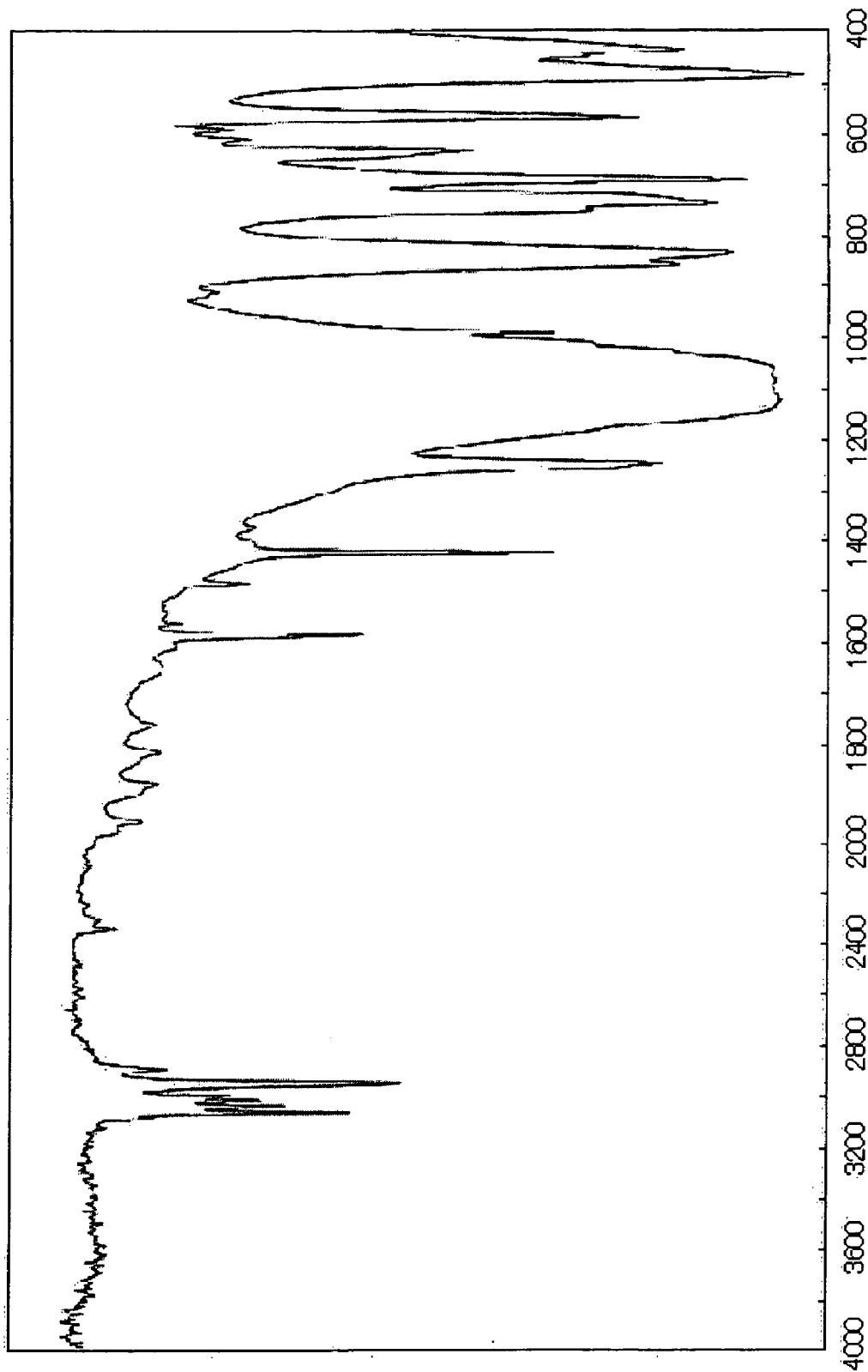
FIG. 5 is an IR spectrum diagram of the organic silicon compound synthesized in Example 4.

The present invention shall specifically be explained below.

The organic silicon compound of the present invention is obtained by using polysilsesquioxane as a raw material, which is obtained by hydrolyzing the silane compound having three hydrolyzable groups and represented by Formula (2) described above, dissolving this in an organic solvent, and then reacting it with an alkaline metal hydroxide to thereby cut a siloxane bond and allow the alkaline metal to coordinate thereto, or by subjecting the trifunctional silane compound to hydrolysis and polycondensation in the presence of a monovalent alkaline metal hydroxide and an organic solvent.

Preferred R in Formulas (1) and (2) represents independently a hydrogen atom, a linear or branched alkyl group having 44 or less carbon atoms, a partially or wholly cyclic alkyl group having 44 or less carbon atoms, a linear or branched alkenyl group having 45 or less carbon atoms, a partially or wholly cyclic alkenyl group having 45 or less carbon atoms, a substituted or non-substituted aryl group, a substituted or non-substituted arylalkyl group, or a substituted or non-substituted arylalkenyl group. At least one hydrogen atom contained in the alkyl group and alkenyl group may be replaced by a fluorine atom, and at least one —CH$_2$—, which is not adjacent, may be replaced by —O—. In alkylene contained in the arylalkyl group, at least one hydrogen atom may be replaced by a fluorine atom and at least one —CH$_2$—, which is not adjacent, may be replaced by —O—. In alkenylene contained in the arylalkenyl group, at least one hydrogen atom may be replaced by a fluorine atom, and at least one —CH$_2$—, which is not adjacent, may be replaced by —O—. These selected R's may be the same or different.

More preferred R in Formulas (1) and (2) represents independently a hydrogen atom, a linear, branched, or partially or wholly cyclic alkyl group having 30 or less carbon atoms (in the alkyl group, at least one hydrogen atom may be replaced by a fluorine atom, and at least one —CH$_2$—, which is not adjacent, may be replaced by —O—), a linear, or partially or wholly cyclic alkenyl group having 22 or less carbon atoms (at least one —CH$_2$— contained in the alkenyl group, which is not adjacent, may be replaced by —O—), a phenyl group, a naphthalenyl group, a linear or branched phenylalkyl group having 17 or less carbon atoms, a partially or wholly cyclic phenylalkyl group having 17 or less carbon atoms, or a linear or branched phenylalkenyl group having 20 or less carbon atoms.

At least one hydrogen atom contained in the phenyl group may be replaced by a fluorine atom, a chlorine atom, a bromine atom, a linear or branched alkyl group having 10 or less carbon atoms, a linear or branched alkenyl group having 4 or less carbon atoms (at least one hydrogen atom contained in the alkenyl group may be replaced by a phenyl group), a linear or branched alkoxy group having 18 or less carbon atoms, a phenoxy group, a phenyl group or a phenylmethyl group. The selected substituents may be the same or different, and when different, they may be any combination of a methyl group and a fluorine atom, a methyl group and a chlorine atom, a methyl group and a bromine atom, an ethenyl group and a fluorine atom, an alkoxy group and a fluorine atom, an alkoxy group and a chlorine atom, and an alkoxy group and a bromine atom.

At least one hydrogen atom in a phenyl group contained in the phenylalkyl group may be replaced by a fluorine atom, a chlorine atom, a bromine atom, a linear, branched, or partially or wholly cyclic alkyl group having 12 or less carbon atoms (at least one hydrogen atom contained in the alkyl group may be replaced by a fluorine atom), a linear alkenyl group having 3 or less carbon atoms, a linear alkoxy group having 10 or less carbon atoms (at least one hydrogen atom contained in the alkoxy group may be replaced by a fluorine atom), a methoxymethyl group, a phenoxy group or a phenyl group. The selected substituents may be the same or different, and when different, they may be any combination of a methyl group and a methoxy group, a methyl group and a chlorine atom, a methyl group and a bromine atom, and a methoxy group and a chlorine atom. At least one —CH$_2$— in alkylene contained in the phenylalkyl group, which is not adjacent, may be replaced by —O—.

At least one hydrogen atom in a phenyl group contained in the phenylalkenyl group may be replaced by a fluorine atom or a methyl group.

And, these selected R's may be the same or different.

Capable of being given as the specific examples of such R are a hydrogen atom, methyl, ethyl, n-propyl, n-butyl, n-pentyl, n-hexyl, n-heptyl, n-octyl, n-nonyl, n-decyl, n-undecyl, n-dodecyl, n-tetradecyl, n-hexadecyl, n-octadecyl, n-eicosyl, n-docosyl and n-triacontyl as the linear alkyl group having 30 or less carbon atoms, 1-methylethyl, 2-methylpropyl, 1,1-dimethylethyl, 1,1,2-trimethylpropyl, 2,4,4-trimethylpentyl and 2-dodecylhexadecyl as the branched alkyl group having 30 or less carbon atoms, and cyclohexylmethyl, adamantaneethyl, cyclopentyl, cyclohexyl, 2-bicycloheptyl and cyclooctyl as the partially or wholly cyclic alkyl group having 30 or less carbon atoms.

Capable of being given are 3,3,3-trifluoropropyl, 3,3,4,4,5,5,6,6,6-nonadecafluorohexyl, tridecafluoro-1,1,2,2-tetrahydrooctyl, heptadecafluoro-1,1,2,2-tetrahydrodecyl, perfluoro-1H,1H,2H,2H-dodecyl and perfluoro-1H,1H,2H,2H-tetradecyl as the alkyl group in which at least one hydrogen atom is replaced by a fluorine atom, and 3-methoxypropyl, methoxyethoxyundecyl and 3-heptafluoroisopropoxypropyl as the alkyl group in which at least one —CH$_2$—, which is not adjacent, is replaced by —O—.

Capable of being given are ethenyl, 2-propenyl, 3-butenyl, 5-hexenyl, 7-octenyl, 10-undecenyl and 21-docosenyl as the linear alkenyl group having 22 or less carbon atoms, 2-(3-cyclohexenyl)ethyl, 5-(bicycloheptenyl)ethyl, 2-cyclopentenyl, 3-cyclohexenyl, 5-norbornene-2-yl and 4-cyclooctenyl as the partially or wholly cyclic alkenyl group having 22 or less carbon atoms, and allyloxyundecyl as the alkenyl group in which at least one —CH$_2$—, which is not adjacent, is replaced by —O—.

Capable of being given are phenyl, pentafluorophenyl, 4-chlorophenyl and 4-bromophenyl as the phenyl group in which at least one hydrogen atom is replaced by a fluorine atom, a chlorine atom or a bromine atom, 4-methylphenyl, 4-ethylphenyl, 4-propylphenyl, 4-butylphenyl, 4-pentylphenyl, 4-heptylphenyl, 4-octylphenyl, 4-nonylphenyl, 4-decylphenyl, 2,4-dimethylphenyl, 2,4,6-trimethylphenyl, 2,4,6-triethylphenyl, 4-(1-methylethyl)phenyl, 4-(1,1-dimethylethyl)phenyl, 4-(2-ethylhexyl)phenyl and 2,4,6-tris(1-methylethyl)phenyl as the phenyl group in which at least one hydrogen atom is replaced by a linear or branched alkyl group having 10 or less carbon atoms, 4-ethenylphenyl, 4-(1-methylethenyl)phenyl and 4-(3-butenyl)phenyl as the phenyl group in which at least one hydrogen atom is replaced by a linear or branched alkenyl group having 4 or less carbon atoms, 4-(2-phenylethenyl)phenyl as the phenyl group in which at least one hydrogen atom in an alkenyl group, which is substituted for at least one hydrogen atom in a phenyl group, is replaced by a phenyl group, and (4-methoxy)phenyl, (4-ethoxy)phenyl, (4-propoxy)phenyl, (4-butoxy)phenyl, (4-pentyloxy)phenyl, (4-heptyloxy)phenyl, (4-decyloxy)phenyl and (4-octadecyloxy)phenyl as the phenyl group in which at least one hydrogen atom is replaced by a linear alkoxy group having 18 or less carbon atoms.

Capable of being given are 4-(1-methylethoxy)phenyl, 4-(2-methylpropoxy)phenyl and 4-(1,1-dimethylethoxy) phenyl as the phenyl group in which at least one hydrogen atom is replaced by a branched alkoxy group having 18 or less carbon atoms, (4-phenoxy)phenyl as the phenyl group in which at least one hydrogen atom is replaced by a phenoxy group, 5',6'-diphenyl(1,1':2',1''-terphenyl)-3'-yl as the phenyl group in which at least one hydrogen atom is replaced by a phenyl group, and (3-phenylmethyl)phenyl as the phenyl group in which at least one hydrogen atom is replaced by a phenylmethyl group. When these selected substituents are different, capable of being given are 3-chloro-4-methylphenyl, 2,5-dichloro-4-methylphenyl, 3,5-dichloro-4-methylphenyl, 2,3,5-trichloro-4-methylphenyl and 2,3,6-trichloro-4-methylphenyl as the phenyl group in which a methyl group is combined with a chlorine atom.

Capable of being given are 3-bromo-4-methylphenyl, 2,5-dibromo-4-methylphenyl and 3,5-dibromo-4-methylphenyl as the phenyl group in which a methyl group is combined with a bromine atom, 2,3-difluoro-4-methylphenyl as the phenyl group in which a methyl group is combined with a fluorine atom, 4-ethenyl-2,3,5,6-tetrafluorophenyl as the phenyl group in which an ethenyl group is combined with a fluorine atom, and 2,3-difluoro-4-methoxyphenyl, 2,3-difluoro-4-ethoxyphenyl and 2,3-difluoro-4-propoxyphenyl as the phenyl group in which an alkoxy group is combined with a fluorine atom.

Capable of being given are 3-chloro-4-methoxyphenyl as the phenyl group in which an alkoxy group is combined with a chlorine atom, 3-bromo-4-methoxyphenyl and 3,5-dibromo-4-methoxyphenyl as the phenyl group in which an alkoxy group is combined with a bromine atom, 1-naphthalenyl, and phenylmethyl, 2-phenylethyl, 3-phenylpropyl, 4-phenylbutyl, 5-phenylpentyl, 6-phenylhexyl and 1-phenylundecyl as the linear phenylalkyl group having 17 or less carbon atoms.

Capable of being given are 1-phenylethyl, 2-phenylpropyl, 1-methyl-2-phenylethyl, 1-phenylpropyl, 3-phenylbutyl, 1-methyl-3-phenylpropyl, 2-phenylbutyl, 2-methyl-2-phenylpropyl and 1-phenylhexyl as the branched phenylalkyl group having 17 or less carbon atoms, and 4-phenylcyclohexyl, 3-phenylcyclohexyl, 4-(phenylmethyl)cyclohexyl and 4-phenylbicyclo[2.2.2]octo-1-yl as the partially or wholly cyclic phenylalkyl group having 17 or less carbon atoms.

Capable of being given are (4-fluorophenyl)methyl, (2,3,4,5,6-pentafluorophenyl)methyl, 2-(2,3,4,5,6-pentafluorophenyl)ethyl and 3-(2,3,4,5,6-pentafluorophenyl)propyl as the linear phenylalkyl group in which at least one hydrogen atom in a phenyl group is replaced by a fluorine atom, and 2-(2-fluorophenyl)propyl and 2-(4-fluorophenyl)propyl as the branched phenylalkyl group in which at least one hydrogen atom in a phenyl group is replaced by a fluorine atom.

Capable of being given are 4-(3-fluorophenyl)bicyclo[2.2.2]octo-1-yl and 4-(4-fluorophenyl)bicyclo[2.2.2]octo-1-yl as the partially or wholly cyclic phenylalkyl group in which at least one hydrogen atom in a phenyl group is replaced by a fluorine atom, and (4-chlorophenyl)methyl, (2-chlorophenyl)methyl, (2,6-dichlorophenyl)methyl, (2,4-dichlorophenyl)methyl, (2,3,6-trichlorophenyl)methyl, (2,4,6-trichlorophenyl)methyl, (2,4,5-trichlorophenyl)methyl, (2,3,4,6-tetrachlorophenyl)methyl, (2,3,4,5,6-pentachlorophenyl)methyl, 2-(2-chlorophenyl)ethyl, 2-(4-chlorophenyl)ethyl, 2-(2,4,5-chlorophenyl)ethyl, 2-(2,3,6-chlorophenyl)ethyl, 3-(3-chlorophenyl)propyl, 3-(4-chlorophenyl)propyl, 3-(2,4,5-trichlorophenyl)propyl, 3-(2,3,6-trichlorophenyl)propyl, 4-(2-chlorophenyl)butyl, 4-(3-chlorophenyl)butyl, 4-(4-chlorophenyl)butyl, 4-(2,3,6-trichlorophenyl)butyl and 4-(2,4,5-trichlorophenyl)butyl as the linear phenylalkyl group in which at least one hydrogen atom in a phenyl group is replaced by a chlorine atom.

Capable of being given are 1-(3-chlorophenyl)ethyl, 1-(4-chlorophenyl)ethyl, 2-(4-chlorophenyl)propyl, 2-(2-chlorophenyl)propyl and 1-(4-chlorophenyl)butyl as the branched phenylalkyl group in which at least one hydrogen atom in a phenyl group is replaced by a chlorine atom, and (2-bromophenyl)methyl, (4-bromophenyl)methyl, (2,4-dibromophenyl)methyl, (2,4,6-tribromophenyl)methyl, (2,3,4,5-tetrabromophenyl)methyl, (2,3,4,5,6-pentabromophenyl)methyl, 2-(4-bromophenyl)ethyl, 3-(4-bromophenyl)propyl, 3-(3-bromophenyl)propyl and 4-(4-bromophenyl)butyl as the linear phenylalkyl group in which at least one hydrogen atom in a phenyl group is replaced by a bromine atom.

Capable of being given are 1-(4-bromophenyl)ethyl, 2-(2-bromophenyl)propyl and 2-(4-bromophenyl)propyl as the branched phenylalkyl group in which at least one hydrogen atom in a phenyl group is replaced by a bromine atom, and (2-methylphenyl)methyl, (3-methylphenyl)methyl, (4-methylphenyl)methyl, (4-dodecylphenyl)methyl, (3,5-dimethylphenyl)methyl, 2-(4-methylphenyl)ethyl, 2-(3-methylphenyl)ethyl, 2-(2,5-dimethylphenyl)ethyl, 2-(4-ethylphenyl)ethyl and 2-(3-ethylphenyl)ethyl as the linear phenylalkyl group in which at least one hydrogen atom in a phenyl group is replaced by a linear alkyl group having 12 or less carbon atoms.

Capable of being given are 1-(4-methylphenyl)ethyl, 1-(3-methylphenyl)ethyl, 1-(2-methylphenyl)ethyl, 2-(4-methylphenyl)propyl, 2-(2-methylphenyl)propyl, 2-(4-ethylphenyl)propyl, 2-(2-ethylphenyl)propyl, 2-(2,3-dimethylphenyl)propyl, 2-(2,5-dimethylphenyl)propyl, 2-(3,5-dimethylphenyl)propyl, 2-(2,4-dimethylphenyl)propyl, 2-(3,4-dimethylphenyl)propyl and 2-(2,5-dimethylphenyl) butyl as the branched phenylalkyl group in which at least one hydrogen atom in a phenyl group is replaced by a linear alkyl group having 12 or less carbon atoms, and (4-(1-methylethyl)phenyl)methyl, 2-(4-(1,1-dimethylethyl)phenyl)ethyl, 2-(4-(1-methylethyl)phenyl)propyl and 2-(3-(1-methylethyl)phenyl)propyl as the linear phenylalkyl group in which at least one hydrogen atom in a phenyl group is replaced by a branched alkyl group having 12 or less carbon atoms.

Capable of being given are (4-tricyclo[3.3.1$^{13,7}$]deca-1-yl-phenyl)methyl and 2-(4-tricyclo[3.3.1$^{13,7}$]deca-1-yl-phenyl)ethyl as the linear phenylalkyl group in which at least one hydrogen atom in a phenyl group is replaced by a partially or wholly cyclic alkyl group having 12 or less carbon atoms, (3-(trifluoromethyl)phenyl)methyl, (2-(4-trifluoromethyl)phenyl)ethyl, (2-(4-nonafluorobutyl)phenyl) ethyl, (2-(4-tridecafluorohexyl)phenyl)ethyl and (2-(4-heptadecafluorooctyl)-phenyl)ethyl as the linear phenylalkyl group in which at least one hydrogen atom in an alkyl group, which is substituted for at least one hydrogen atom in a phenyl group, is replaced by a fluorine atom, and (1-(3-trifluoromethyl)phenyl)ethyl, (1-(4-trifluoromethyl)phenyl)

ethyl, (1-(4-nonafluorobutyl)phenyl)ethyl, (1-(4-tridecafluorohexyl)phenyl)ethyl, (1-(4-heptadecafluorooctyl)phenyl)ethyl, (2-(4-nonafluorobutyl)phenyl)propyl, 1-methyl-1-(4-nonafluorobutyl)phenyl)ethyl, (2-(4-tridecafluorohexyl)phenyl)propyl, 1-methyl-1-(4-tridecafluorohexyl)phenyl)ethyl, (2-(4-heptadecafluorooctyl)phenyl)propyl and 1-methyl-1-(4-heptadecafluorooctyl)phenyl)ethyl as the branched phenylalkyl group in which at least one hydrogen atom in an alkyl group, which is substituted for at least one hydrogen atom in a phenyl group, is replaced by a fluorine atom.

Capable of being given are (2-(4-ethenyl)phenyl)ethyl, (1-(4-ethenyl)phenyl)ethyl and 1-(2-(2-propenyl)phenyl)ethyl as the linear or branched phenylalkyl group in which at least one hydrogen atom in a phenyl group is replaced by a linear alkenyl group having 3 or less carbon atoms, and (4-methoxyphenyl)methyl, (3-methoxyphenyl)methyl, (4-ethoxyphenyl)methyl, 2-(4-methoxyphenyl)ethyl, 3-(4-methoxyphenyl)propyl, 3-(2-methoxyphenyl)propyl, 3-(3,4-dimethoxyphenyl)propyl, 11-(4-methoxyphenyl)undecyl and 1-(4-methoxyphenyl)ethyl as the linear phenylalkyl group in which at least one hydrogen atom in a phenyl group is replaced by a linear or branched alkoxy group having 10 or less carbon atoms.

Capable of being given are 3-(2-nonadecafluorodecenyloxyphenyl)propyl as the phenylalkyl group in which at least one hydrogen atom in an alkoxy group, which is substituted for at least one hydrogen atom in a phenyl group, is replaced by a fluorine atom, (3-(methoxymethyl)phenyl)ethyl as the linear phenylalkyl group in which at least one hydrogen atom in a phenyl group is replaced by a methoxymethyl group, and 2-(4-phenoxyphenyl)ethyl, 2-(4-phenoxyphenyl)propyl and 2-(2-phenoxyphenyl)propyl as the linear or branched phenylalkyl group in which at least one hydrogen atom in a phenyl group is replaced by a phenoxy group.

Capable of being given are (1,1'-biphenyl)-4-yl-methyl, 2-(1,1'-biphenyl)-3-yl-ethyl, 2-(1,1'-biphenyl)-4-yl-ethyl, 3-(1,1'-biphenyl)-4-yl-propyl, (5',6'-diphenyl(1,1':2',1'-terphenyl)-3'-yl)methyl, 2-(1,1'-biphenyl)-2-yl-propyl and 2-(1,1'-biphenyl)-4-yl-propyl as the linear or branched phenylalkyl group in which at least one hydrogen atom in a phenyl group is replaced by a phenyl group, 3-(2,5-dimethoxy-(3,4,6-trimethyl)phenyl)propyl as the phenylalkyl group in which a methyl group and a methoxy group are combined when these selected substituents are different, and (3-chloro-(2-methyl)phenyl)methyl, (4-chloro-(2-methyl)phenyl)methyl, (5-chloro-(2-methyl)phenyl)methyl, (6-chloro-(2-methyl)phenyl)methyl, (2-chloro-(4-methyl)phenyl)methyl, (3-chloro-(4-methyl)phenyl)methyl, (2,3-dichloro-(4-methyl)phenyl)methyl, (2,5-dichloro-(4-methyl)phenyl)methyl, (3,5-dichloro-(4-methyl)phenyl)methyl, (2,3,5-trichloro-(4-methyl)phenyl)methyl, (2,3,5,6-tetrachloro-(4-methyl)phenyl)methyl, (2,3,4,6-tetrachloro-(5-methyl)phenyl)methyl, (2,3,4,5-tetrachloro-(6-methyl)phenyl)methyl, (4-chloro-(3,5-dimethyl)phenyl)methyl, (2-chloro-(3,5-dimethyl)phenyl)methyl, (2,4-dichloro-(3,5-dimethyl)phenyl)methyl, (2,6-dichloro-(3,5-dimethyl)phenyl)methyl and (2,4,6-trichloro-(3,5-dimethyl)phenyl)methyl as the phenylalkyl group in which a methyl group and a chlorine atom are combined.

Capable of being given are (3-bromo-(2-methyl)phenyl)methyl, (4-bromo-(2-methyl)phenyl)methyl, (5-bromo-(2-methyl)phenyl)methyl, (6-bromo-(2-methyl)phenyl)methyl, (3-bromo-(4-methyl)phenyl)methyl, (2,3-dibromo-(4-methyl)phenyl)methyl, (2,3,5-tribromo-(4-methyl)phenyl)methyl and (2,3,5,6-tetrabromo-(4-methyl)phenyl)methyl as the phenylalkyl group in which a methyl group and a bromine atom are combined, and 11-(3-chloro-4-methoxyphenyl)undecyl as the phenylalkyl group in which a methoxy group and a chlorine atom are combined.

Capable of being given are 3-phenoxypropyl as the phenylalkyl group in which at least one —$CH_2$— in alkylene, which is not adjacent, is replaced by —O—, (2-phenyl)ethenyl, 3-phenyl-2-propenoyl and 14-phenyl-13-tetradecenoyl as the linear phenylalkenyl group having 20 or less carbon atoms, and (1-phenyl)ethenyl and 4-phenyl-4-pentenoyl as the branched phenylalkenyl group having 20 or less carbon atoms.

Capable of being given are 2-(2,3,4,5,6-pentafluorophenyl)ethenyl as the phenylalkenyl group in which at least one hydrogen atom in a phenyl group is replaced by a fluorine atom, and 2-(4-methylphenyl)ethenyl as the phenylalkenyl group in which at least one hydrogen atom in a phenyl group is replaced by a methyl group. These selected R's may be the same or different.

To specifically give the examples of the trichlorosilanes and the trialkoxysilanes which are silane compounds having R described above and three hydrolyzable groups, capable of being given are trichlorosilane as the trichlorosilanes having a hydrogen atom, trimethoxysilane, triethoxysilane and triisopropoxysilane as the trialkoxysilanes having a hydrogen atom, and methyltrichlorosilane, ethyltrichlorosilane, n-propyltrichlorosilane, n-butyltrichlorosilane, n-pentyltrichlorosilane, n-hexyltrichlorosilane, n-heptyltrichlorosilane, n-octyltrichlorosilane, n-nonyltrichlorosilane, n-decyltrichlorosilane, n-undecyltrichlorosilane, n-dodecyltrichlorosilane, n-tetradecyltrichlorosilane, n-hexadecyltrichlorosilane, n-octadecyltrichlorosilane, n-eicosyltrichlorosilane, n-docosyltrichlorosilane and n-triacontyltrichlorosilane as the trichlorosilanes having a linear alkyl group having 30 or less carbon atoms.

Capable of being given are methyltrimethoxysilane, methyltriethoxysilane, methyltripropoxysilane, ethyltrimethoxysilane, ethyltriethoxysilane, n-propyltrimethoxysilane, n-propyltriethoxysilane, n-butyltrimethoxysilane, n-pentyltriethoxysilane, n-hexyltrimethoxysilane, n-hexyltriethoxysilane, n-octyltrimethoxysilane, n-octyltriethoxysilane, n-decyltrimethoxysilane, n-decyltriethoxysilane, n-dodecyltrimethoxysilane, n-dodecyltriethoxysilane, n-hexadecyltrimethoxysilane, n-hexadecyltriethoxysilane, n-octadecyltrimethoxysilane and n-octadecyltriethoxysilane as the trialkoxysilanes having a linear alkyl group having 30 or less carbon atoms.

Capable of being given are 1-methylethyltrichlorosilane, 2-methylpropyltrichlorosilane, 1,1-dimethylethyltrichlorosilane, 1,1,2-trimethylpropyltrichlorosilane, 2,4,4-trimethylpentyltrichlorosilane and 2-dodecylhexadecyltrichlorosilane as the trichlorosilanes having a branched alkyl group having 30 or less carbon atoms, and 2-methylpropyltrimethoxysilane and 2,4,4-trimethylpentyltrimethoxysilane as the trialkoxysilanes having a branched alkyl group having 30 or less carbon atoms.

Capable of being given are cyclohexylmethyltrichlorosilane, adamantaneethyltrichlorosilane, cyclopentyltrichlorosilane, cyclohexyltrichlorosilane, 2-bicycloheptyltrichlorosilane and cyclooctyltrichlorosilane as the trichlorosilanes having a partially or wholly cyclic alkyl group having 30 or less carbon atoms, and cyclopentyltrimethoxysilane and cyclohexyltrimethoxysilane as the trialkoxysilanes having a wholly cyclic alkyl group having 30 or less carbon atoms.

Capable of being given are (3,3,3-trifluoropropyl)trichlorosilane, (3,3,4,4,5,5,6,6,6-nonadecafluorohexyl)trichlorosilane, (tridecafluoro-1,1,2,2-tetrahydrooctyl)trichlorosilane and (heptadecafluoro-1,1,2,2-tetrahydrodecyl)trichlorosilane as the trichlorosilanes having an alkyl group in which at least one hydrogen atom is replaced by a fluorine atom, perfluorododecyl-1H,1H,2H,2H-triethoxysilane and perfluorotetradecyl-1H,1H,2H,2H-triethoxysilane as the trialkoxysilanes having an alkyl group in which at least one hydrogen atom is replaced by a fluorine atom, methoxyethoxyundecyltrichlorosilane and (3-heptafluoroisopropoxypropyl)trichlorosilane as the trichlorosilanes having an alkyl group in which at least one —$CH_2$—, which is not adjacent, is replaced by —O—, and 3-methoxypropyltrimethoxysilane as the trialkoxysilanes having an alkyl group in which at least one —$CH_2$—, which is not adjacent, is replaced by —O—.

Capable of being given are ethenyltrichlorosilane, 2-propenyltrichlorosilane, 5-hexenyltrichlorosilane, 7-octenyltrichlorosilane and 10-undecenyltrichlorosilane as the trichlorosilanes having a linear alkenyl group having 22 or less carbon atoms and ethenyltrimethoxysilane, ethenyltriethoxysilane, tris(1-methylethoxy)ethenylsilane, tris(1-methylpropoxy)ethenylsilane, tris(1,1-dimethylethoxy)ethenylsilane, 2-propenyltrimethoxysilane, 2-propenyltriethoxysilane, 3-butenyl-triethoxysilane, 5-hexenyltrimethoxysilane, 7-octenyltrimethoxysilane and 21-docosenyltriethoxysilane as the trialkoxysilanes having a linear alkenyl group having 22 or less carbon atoms.

Capable of being given are (2-(3-cyclohexenyl)ethyl)trichlorosilane, (5-(bicycloheptenyl)ethyl)trichlorosilane, 2-cyclopentenyltrichlorosilane, 3-cyclohexenyltrichlorosilane, trichloro(5-norbornene-2-yl)silane and 4-cyclooctenyltrichlorosilane as the trichlorosilanes having a partially or wholly cyclic alkenyl group having 22 or less carbon atoms, and triethoxy(5-norbornene-2-yl)silane as the trialkoxysilanes having a wholly cyclic alkenyl group having 22 or less carbon atoms.

Capable of being given are allyloxyundecyltrimethoxysilane as the trialkoxysilanes having an alkenyl group in which at least one —$CH_2$—, which is not adjacent, is replaced by —O—, phenyltrichlorosilane as the trichlorosilanes having a phenyl group, and phenyltrimethoxysilane and phenyltriethoxysilane as the trialkoxysilanes having a phenyl group.

Capable of being given are pentafluorophenyltriethoxysilane as the trialkoxysilanes having a phenyl group in which at least one hydrogen atom is replaced by a fluorine atom, 4-chlorophenylnyltrichlorosilane as the trichlorosilanes having a phenyl group in which at least one hydrogen atom is replaced by a chlorine atom, 4-chlorophenyltriethoxysilane as the trialkoxysilanes having a phenyl group in which at least one hydrogen atom is replaced by a chlorine atom, and 4-bromophenyltrichlorosilane as the trichlorosilanes having a phenyl group in which at least one hydrogen atom is replaced by a bromine atom.

Capable of being given are 4-bromophenyltrimethoxysilane as the trialkoxysilanes having a phenyl group in which at least one hydrogen atom is replaced by a bromine atom, (4-methylphenyl)trichlorosilane, (4-ethylphenyl)trichlorosilane, (4-propylphenyl)trichlorosilane, (4-butylphenyl)trichlorosilane, (4-pentylphenyl)trichlorosilane, (4-nonylphenyl)trichlorosilane, (2,4,6-trimethylphenyl)trichlorosilane and (2,4,6-triethylphenyl)trichlorosilane as the trichlorosilanes having a phenyl group in which at least one hydrogen atom is replaced by a linear alkyl group having 10 or less carbon atoms, and (4-methylphenyl)trimethoxysilane, (4-ethylphenyl)trimethoxysilane, (4-propylphenyl)trimethoxysilane, (4-pentylphenyl)trimethoxysilane, (4-pentylphenyl)triethoxysilane, (4-heptylphenyl)triethoxysilane, (4-octylphenyl)trimethoxysilane, (4-decylphenyl)triethoxysilane, (2,4-dimethylphenyl)triethoxysilane, (2,4,6-trimethylphenyl)trimethoxysilane and (2,4,6-trimethylphenyl)triethoxysilane as the trialkoxysilanes having a phenyl group in which at least one hydrogen atom is replaced by a linear alkyl group having 10 or less carbon atoms.

Capable of being given are (4-(1-methylethyl)phenyl)trichlorosilane, (4-(1,1-dimethylethyl)phenyl)trichlorosilane and (2,4,6-tris(1-methylethyl)phenyl)trichlorosilane as the trichlorosilanes having a phenyl group in which at least one hydrogen atom is replaced by a branched alkyl group having 10 or less carbon atoms, and (4-(1-methylethyl)phenyl)trimethoxysilane, (4-(1,1-dimethylethyl)phenyl)trimethoxysilane and (4-(2-ethylhexyl)phenyl)trimethoxysilane as the trialkoxysilanes having a phenyl group in which at least one hydrogen atom is replaced by a branched alkyl group having 10 or less carbon atoms.

Capable of being given are (4-ethenylphenyl)trichlorosilane as the trichlorosilanes having a phenyl group in which at least one hydrogen atom is replaced by a linear alkenyl group having 4 or less carbon atoms, (4-ethenylphenyl)triethoxysilane as the trialkoxysilanes having a phenyl group in which at least one hydrogen atom is replaced by a linear alkenyl group having 4 or less carbon atoms, (4-(1-methylethenyl)phenyl)trichlorosilane as the trichlorosilanes having a phenyl group in which at least one hydrogen atom is replaced by a branched alkenyl group having 4 or less carbon atoms, and (4-(3-butenyl)phenyl)trimethoxysilane and (4-(1-methylethenyl)phenyl)triethoxysilane as the trialkoxysilanes having a phenyl group in which at least one hydrogen atom is replaced by a branched alkenyl group having 4 or less carbon atoms.

Capable of being given are (4-(2-phenylethenyl)phenyl)triethoxysilane as the trialkoxysilanes having a phenyl group in which at least one hydrogen atom in an alkenyl group, which is substituted for at least one hydrogen atom in the phenyl group, is replaced by a phenyl group, (4-ethoxyphenyl)trichlorosilane, (4-propoxyphenyl)trichlorosilane and (4-octadecyloxyphenyl)trichlorosilane as the trichlorosilanes having a phenyl group in which at least one hydrogen atom is replaced by a linear alkoxy group having 18 or less carbon atoms, and (4-methoxyphenyl)trimethoxysilane, (4-methoxyphenyl)triethoxysilane, (4-butoxyphenyl)trimethoxysilane, (4-pentyloxyphenyl)trimethoxysilane, (4-heptyloxyphenyl)triethoxysilane and (4-decyloxyphenyl)triethoxysilane as the trialkoxysilanes having a phenyl group in which at least one hydrogen atom is replaced by a linear alkoxy group having 18 or less carbon atoms.

Capable of being given are (4-(1-methylethoxy)phenyl)trichlorosilane and (4-(2-methylpropoxy)phenyl)trichlorosilane as the trichlorosilanes having a phenyl group in which at least one hydrogen atom is replaced by a branched alkoxy group having 18 or less carbon atoms, (4-(1,1-dimethylethoxy)phenyl)triethoxysilane as the trialkoxysilanes having a phenyl group in which at least one hydrogen atom is replaced by a branched alkoxy group having 18 or less carbon atoms, and (4-phenoxyphenyl)trichlorosilane as the trichlorosilanes having a phenyl group in which at least one hydrogen atom is replaced by a phenoxy group.

Capable of being given are (5',6'-diphenyl(1,1':2',1"-terphenyl)-3'-yl)triethoxysilane as the trialkoxysilanes having a phenyl group in which at least one hydrogen atom is replaced by a phenyl group, ((3-phenylmethyl)phenyl)trichlorosilane as the trichlorosilanes having a phenyl group in which at least one hydrogen atom is replaced by a phenylmethyl group, and (2,3-difluoro-4-methylphenyl)trimethoxysilane as the trialkoxysilanes having a phenyl group in which a methyl group is combined with a fluorine atom when these selected substituents are different.

Capable of being given are (3-chloro-4-methylphenyl)trichlorosilane, (2,5-dichloro-4-methylphenyl)trichlorosilane, (3,5-dichloro-4-methylphenyl)trichlorosilane, (2,3,5-trichloro-4-methylphenyl)trichlorosilane and (2,3,6-trichloro-4-methylphenyl)trichlorosilane as the trichlorosilanes having a phenyl group in which a methyl group is combined with a chlorine atom, and (3-bromo-4-methylphenyl)trichlorosilane, (2,5-dibromo-4-methylphenyl)trichlorosilane and (3,5-dibromo-4-methylphenyl)trichlorosilane as the trichlorosilanes having a phenyl group in which a methyl group is combined with a bromine atom.

Capable of being given are (4-ethenyl-2,3,5,6-tetrafluorophenyl)trimethoxysilane and (4-ethenyl-2,3,5,6-tetrafluorophenyl)triethoxysilane as the trialkoxysilanes having a phenyl group in which an ethenyl group is combined with a fluorine atom, and (2,3-difluoro-4-methoxyphenyl)trimethoxysilane, (2,3-difluoro-4-ethoxyphenyl)trimethoxysilane and (2,3-difluoro-4-propoxyphenyl)trimethoxysilane as the trialkoxysilanes having a phenyl group in which an alkoxy group is combined with a fluorine atom.

Capable of being given are (3-chloro-4-methoxyphenyl)trichlorosilane as the trichlorosilanes having a phenyl group in which an alkoxy group is combined with a chlorine atom, and (3-bromo-4-methoxyphenyl)trichlorosilane and (3,5-dibromo-4-methoxyphenyl)trichlorosilane as the trichlorosilanes having a phenyl group in which an alkoxy group is combined with a bromine atom.

Capable of being given are (1-naphthalenyl)trimethoxysilane and (1-naphthalenyl)triethoxysilane as the trialkoxysilanes having a naphthalenyl group, (phenylmethyl)trichlorosilane, (2-phenylethyl)trichlorosilane, (3-phenylpropyl)trichlorosilane, (4-phenylbutyl)trichlorosilane, (5-phenylpentyl)trichlorosilane, (6-phenylhexyl)trichlorosilane and (11-phenylundecyl)trichlorosilane as the trichlorosilanes having a linear phenylalkyl group having 17 or less carbon atoms, and (2-phenylethyl)trimethoxysilane and (phenylmethyl)triethoxysilane as the trialkoxysilanes having a linear phenylalkyl group having 17 or less carbon atoms.

Capable of being given are (1-phenylethyl)trichlorosilane, (2-phenylpropyl)trichlorosilane, 1-methyl(2-phenylethyl)trichlorosilane, (1-phenylpropyl)trichlorosilane, (3-phenylbutyl)trichlorosilane, 1-methyl(3-phenylpropyl)trichlorosilane, (2-phenylbutyl)trichlorosilane, 2-methyl(2-phenylpropyl)trichlorosilane and (1-phenylhexyl)trichlorosilane as the trichlorosilanes having a branched phenylalkyl group having 17 or less carbon atoms, and (4-phenylcyclohexyl)trichlorosilane, (3-phenylcyclohexyl)trichlorosilane, (4-(phenylmethyl)cyclohexyl)trichlorosilane and (4-(phenylbicyclo[2.2.2]oct-1-yl)trichlorosilane as the trichlorosilanes having a partially or wholly cyclic phenylalkyl group having 17 or less carbon atoms.

Capable of being given are (4-(phenylbicyclo-[2.2.2]oct-1-yl)triethoxysilane as the trialkoxysilanes having a partially or wholly cyclic phenylalkyl group having 17 or less carbon atoms, and ((4-fluorophenyl)methyl)trichlorosilane, ((2,3,4,5,6-pentafluorophenyl)methyl)trichlorosilane, (2-(2,3,4,5,6-pentafluorophenyl)ethyl)trichlorosilane and (3-(2,3,4,5,6-pentafluorophenyl)propyl)trichlorosilane as the trichlorosilanes having a linear phenylalkyl group in which at least one hydrogen atom in a phenyl group is replaced by a fluorine atom.

Capable of being given are (2-(2-fluorophenyl)propyl)trichlorosilane and (2-(4-fluorophenyl)propyl)trichlorosilane as the trichlorosilanes having a branched phenylalkyl group in which at least one hydrogen atom in a phenyl group is replaced by a fluorine atom, and (4-(3-fluorophenyl)bicyclo[2.2.2]oct-1-yl)trichlorosilane and (4-(4-fluorophenyl)bicyclo[2.2.2]oct-1-yl)trichlorosilane as the trichlorosilanes having a partially or wholly cyclic phenylalkyl group in which at least one hydrogen atom in a phenyl group is replaced by a fluorine atom.

Capable of being given are (4-(3-fluorophenyl)bicyclo[2.2.2]oct-1-yl)triethoxysilane and (4-(4-fluorophenyl)bicyclo[2.2.2]oct-1-yl)triethoxysilane as the trialkoxysilanes having a partially or wholly cyclic phenylalkyl group in which at least one hydrogen atom in a phenyl group is replaced by a fluorine atom, and ((4-chlorophenyl)methyl)trichlorosilane, ((2-chlorophenyl)methyl)trichlorosilane, ((2,6-dichlorophenyl)methyl)trichlorosilane, ((2,4-dichlorophenyl)methyl)trichlorosilane, ((2,3,6-trichlorophenyl)methyl)trichlorosilane, ((2,4,6-trichlorophenyl)methyl)trichlorosilane, ((2,4,5-trichlorophenyl)methyl)trichlorosilane, ((2,3,4,6-tetrachlorophenyl)methyl)trichlorosilane, ((2,3,4,5,6-pentachlorophenyl)methyl)trichlorosilane, (2-(2-chlorophenyl)ethyl)trichlorosilane, (2-(4-chlorophenyl)ethyl)trichlorosilane, (2-(2,4,5-chlorophenyl)ethyl)trichlorosilane, (2-(2,3,6-chlorophenyl)ethyl)trichlorosilane, (3-(3-chlorophenyl)propyl)trichlorosilane, (3-(4-chlorophenyl)propyl)trichlorosilane, (3-(2,4,5-trichlorophenyl)propyl)trichlorosilane, (3-(2,3,6-trichlorophenyl)propyl)trichlorosilane, (4-(2-chlorophenyl)butyl)trichlorosilane, (4-(3-chlorophenyl)butyl)trichlorosilane, (4-(4-chlorophenyl)butyl)trichlorosilane, (4-(2,3,6-trichlorophenyl)butyl)trichlorosilane and (4-(2,4,5-trichlorophenyl)butyl)trichlorosilane as the trichlorosilanes having a linear phenylalkyl group in which at least one hydrogen atom in a phenyl group is replaced by a chlorine atom.

Capable of being given are (1-(3-chlorophenyl)ethyl)trichlorosilane, (1-(4-chlorophenyl)ethyl)trichlorosilane, (2-(4-chlorophenyl)propyl)trichlorosilane, (2-(2-chlorophenyl)propyl)trichlorosilane and (1-(4-chlorophenyl)butyl)trichlorosilane as the trichlorosilanes having a branched phenylalkyl group in which at least one hydrogen atom in a phenyl group is replaced by a chlorine atom, and ((2-bromophenyl)methyl)trichlorosilane, ((4-bromophenyl)methyl)trichlorosilane, ((2,4-dibromophenyl)methyl)trichlorosilane, ((2,4,6-tribromophenyl)methyl)trichlorosilane, ((2,3,4,5-tetrabromophenyl)methyl)trichlorosilane, ((2,3,4,5,6-pentabromophenyl)methyl)trichlorosilane, (2-(4-bromophenyl)ethyl)trichlorosilane, (3-(4-bromophenyl)propyl)trichlorosilane, (3-(3-bromophenyl)propyl)trichlorosilane and (4-(4-bromophenyl)butyl)trichlorosilane as the trichlorosilanes having a linear phenylalkyl group in which at least one hydrogen atom in a phenyl group is replaced by a bromine atom.

Capable of being given are (1-(4-bromophenyl)ethyl)trichlorosilane, (2-(2-bromophenyl)propyl)trichlorosilane and (2-(4-bromophenyl)propyl)trichlorosilane as the trichlorosilanes having a branched phenylalkyl group in which at least one hydrogen atom in a phenyl group is replaced by a bromine atom, and ((2-methylphenyl)methyl)trichlorosilane, ((3-methylphenyl)methyl)trichlorosilane, ((4-methylphenyl)methyl)trichlorosilane, ((4-dodecylphenyl)methyl)trichlorosilane, ((3,5-dimethylphenyl)methyl)trichlorosilane, (2-(4-methylphenyl)ethyl)trichlorosilane, (2-(3-methylphenyl)ethyl)trichlorosilane and (2-(2,5-dimethylphenyl)ethyl)trichlorosilane as the trichlorosilanes having a linear phenylalkyl group in which at least one hydrogen atom in a phenyl group is replaced by a linear alkyl group having 12 or less carbon atoms.

Capable of being given are (2-(4-ethylphenyl)ethyl)trimethoxysilane and (2-(3-ethylphenyl)ethyl)trimethoxysilane as the trialkoxysilanes having a linear phenylalkyl group in which at least one hydrogen atom in a phenyl group is replaced by a linear alkyl group having 12 or less carbon atoms, and (1-(4-methylphenyl)ethyl)trichlorosilane, (1-(3-methylphenyl)ethyl)trichlorosilane, (1-(2-methylphenyl)ethyl)trichlorosilane, (2-(4-methylphenyl)propyl)trichlorosilane, (2-(2-methylphenyl)propyl)trichlorosilane, (2-(4-ethylphenyl)propyl)trichlorosilane, (2-(2-ethylphenyl)propyl)trichlorosilane, (2-(2,3-dimethylphenyl)propyl)trichlorosilane, (2-(2,5-dimethylphenyl)propyl)trichlorosilane, (2-(3,5-dimethylphenyl)propyl)trichlorosilane, (2-(2,4-dimethylphenyl)propyl)trichlorosilane, (2-(3,4-dimethylphenyl)propyl)trichlorosilane and (2-(2,5-dimethylphenyl)butyl)trichlorosilane as the trichlorosilanes having a branched phenylalkyl group in which at least one hydrogen atom in a phenyl group is replaced by a linear alkyl group having 12 or less carbon atoms.

Capable of being given are ((4-(1-methylethyl)phenyl)methyl)trichlorosilane, (2-(4-(1,1-dimethylethyl)phenyl)ethyl)trichlorosilane, (2-(4-(1-methylethyl)phenyl)propyl)trichlorosilane and (2-(3-(1-methylethyl)phenyl)propyl)trichlorosilane as the trichlorosilanes having a linear phenylalkyl group in which at least one hydrogen atom in a phenyl group is replaced by a branched alkyl group having 12 or less carbon atoms, and ((4-tricyclo[3.3.1$^{13,7}$]deca-1-yl-phenyl)methyl)trichlorosilane and (2-(4-tricyclo[3.3.1$^{13,7}$]deca-1-yl-phenyl)ethyl)trichlorosilane as the trichlorosilanes having a linear phenylalkyl group in which at least one hydrogen atom in a phenyl group is replaced by a partially or wholly cyclic alkyl group having 12 or less carbon atoms.

Capable of being given are ((3-trifluoromethylphenyl)methyl)trichlorosilane, (2-(4-trifluoromethylphenyl)ethyl)trichlorosilane, (2-(4-nonafluorobutylphenyl)ethyl)trichlorosilane, (2-(4-tridecafluorohexylphenyl)ethyl)trichlorosilane and (2-(4-heptadecafluorooctylphenyl)ethyl)trichlorosilane as the trichlorosilanes having a linear phenylalkyl group in which at least one hydrogen atom in an alkyl group, which is substituted for at least one hydrogen atom in a phenyl group, is replaced by a fluorine atom, and (1-(3-trifluoromethylphenyl)ethyl)trichlorosilane, (1-(4-trifluoromethylphenyl)ethyl)trichlorosilane, (1-(4-nonafluorobutylphenyl)ethyl)trichlorosilane, (1-(4-tridecafluorohexylphenyl)ethyl)trichlorosilane, (1-(4-heptadecafluorooctylphenyl)ethyl)trichlorosilane, (2-(4-nonafluorobutylphenyl)propyl)trichlorosilane, (1-methyl-1-(4-(nonafluorobutyl)phenyl)ethyl)trichlorosilane, ((2-(4-tridecafluorohexyl)phenyl)-propyl)trichlorosilane, (1-methyl-1-(4-(tridecafluorohexyl)phenyl)ethyl)trichlorosilane, ((2-(4-heptadecafluorooctyl)phenyl)propyl)trichlorosilane and (1-methyl-1-(4-(heptadecafluorooctyl)phenyl)ethyl)trichlorosilane as the trichlorosilanes having a branched phenylalkyl group in which at least one hydrogen atom in an alkyl group, which is substituted for at least one hydrogen atom in a phenyl group, is replaced by a fluorine atom.

Capable of being given are ((2-(4-ethenyl)phenyl)ethyl)trichlorosilane as the trichlorosilanes having a linear phenylalkyl group in which at least one hydrogen atom in a phenyl group is replaced by a linear alkenyl group having 3 or less carbon atoms, ((2-(4-ethenyl)phenyl)ethyl)trimethoxysilane as the trialkoxysilanes having a linear phenylalkyl group in which at least one hydrogen atom in a phenyl group is replaced by a linear alkenyl group having 3 or less carbon atoms, and ((1-(4-ethenyl)phenyl)ethyl)trichlorosilane and (1-(2-(2-propenyl)phenyl)ethyl)trichlorosilane as the trichlorosilanes having a branched phenylalkyl group in which at least one hydrogen atom in a phenyl group is replaced by a linear alkenyl group having 3 or less carbon atoms.

Capable of being given are ((1-(4-ethenyl)phenyl)ethyl)trimethoxysilane as the trialkoxysilanes having a branched phenylalkyl group in which at least one hydrogen atom in a phenyl group is replaced by a branched alkenyl group having 3 or less carbon atoms, and ((4-methoxyphenyl)methyl)trichlorosilane, ((3-methoxyphenyl)methyl)trichlorosilane, ((4-ethoxyphenyl)methyl)trichlorosilane, (2-(4-methoxyphenyl)ethyl)trichlorosilane, (3-(4-methoxyphenyl)propyl)trichlorosilane, (3-(2-methoxyphenyl)propyl)trichlorosilane, (3-(3,4-dimethoxyphenyl)propyl)trichlorosilane and (11-(4-methoxyphenyl)undecyl)trichlorosilane as the trichlorosilanes having a linear phenylalkyl group in which at least one hydrogen atom in a phenyl group is replaced by a linear alkoxy group having 10 or less carbon atoms.

Capable of being given are (1-(4-methoxyphenyl)ethyl)trichlorosilane as the trichlorosilanes having a branched phenylalkyl group in which at least one hydrogen atom in a phenyl group is replaced by a linear alkoxy group having 10 or less carbon atoms, (3-((2-nonadecafluorodecenyloxy)phenyl)propyl)trichlorosilane as the trichlorosilanes having a phenylalkyl group in which at least one hydrogen atom in an alkoxy group substituted for at least one hydrogen atom in a phenyl group is replaced by a fluorine atom, and ((3-(methoxymethyl)phenyl)ethyl)trichlorosilane as the trichlorosilanes having a phenylalkyl group in which at least one hydrogen atom in a phenyl group is replaced by a methoxymethyl group.

Capable of being given are (2-(4-phenoxyphenyl)ethyl)trichlorosilane, (2-(4-phenoxyphenyl)propyl)trichlorosilane and (2-(2-phenoxyphenyl)propyl)trichlorosilane as the trichlorosilanes having a linear or branched phenylalkyl group in which at least one hydrogen atom in a phenyl group is replaced by a phenoxy group, and ((1,1'-biphenyl)-4-yl-methyl)trichlorosilane, (2-(1,1'-biphenyl)-3-yl-ethyl)trichlorosilane, (2-(1,1'-biphenyl)-4-yl-ethyl)trichlorosilane, (3-(1,1'-biphenyl)-4-yl-propyl)trichlorosilane, (2-(1,1'-biphenyl)-2-yl-propyl)trichlorosilane and (2-(1,1'-biphenyl)-4-yl-propyl)trichlorosilane as the trichlorosilanes having a linear or branched phenylalkyl group in which at least one hydrogen atom in a phenyl group is replaced by a phenyl group.

Capable of being given are ((5',6'-diphenyl(1,1':2',1'-terphenyl)-3'-yl)methyl)triethoxysilane as the trialkoxysilanes having a linear phenylalkyl group in which at least one hydrogen atom in a phenyl group is replaced by a phenyl group, (3-(2,5-dimethoxy-(3,4,6-trimethyl)phenyl)propyl)trichlorosilane as the trichlorosilanes having a phenylalkyl group in which a methyl group is combined with a methoxy group when these selected substituents are different, and ((3-chloro-(2-methyl)phenyl)methyl)trichlorosilane, ((4-chloro-(2-methyl)phenyl)methyl)trichlorosilane, ((5-chloro-(2-methyl)phenyl)methyl)trichlorosilane, ((6-chloro-(2-methyl)phenyl)methyl)trichlorosilane, ((2-chloro-(4-methyl)phenyl)methyl)trichlorosilane, ((3-chloro-(4-methyl)phenyl)methyl)trichlorosilane, ((2,3-dichloro-(4-methyl)phenyl)methyl)trichlorosilane, ((2,5-dichloro-(4-methyl)phenyl)methyl)trichlorosilane, ((3,5-dichloro-(4-methyl)phenyl)methyl)trichlorosilane, ((2,3,5-trichloro-(4-methyl)phenyl)methyl)trichlorosilane, ((2,3,5,6-tetrachloro-(4-methyl)phenyl)methyl)trichlorosilane, ((2,3,4,6-tetrachloro-(5-methyl)phenyl)methyl)trichlorosilane, ((2,3,4,5-tetrachloro-(6-methyl)phenyl)methyl)trichlorosilane, ((4- chloro-(3,5-dimethyl)phenyl)methyl)trichlorosilane, ((2-chloro-(3,5-dimethyl)phenyl)methyl)trichlorosilane, ((2,4-dichloro-(3,5-dimethyl)phenyl)methyl)trichlorosilane, ((2,6-dichloro-(3,5-dimethyl)phenyl)methyl)trichlorosilane and ((2,4,6-trichloro-(3,5-dimethyl)phenyl)methyl)trichlorosilane as the trichlorosilanes having a phenylalkyl group in which a methyl group is combined with a chlorine atom.

Capable of being given are ((3-bromo-(2-methyl)phenyl)methyl)trichlorosilane, ((4-bromo-(2-methyl)phenyl)methyl)trichlorosilane, ((5-bromo-(2-methyl)phenyl)methyl)trichlorosilane, ((6-bromo-(2-methyl)phenyl)methyl)trichlorosilane, ((3-bromo-(4-methyl)phenyl)methyl)trichlorosilane, ((2,3-dibromo-(4-methyl)phenyl)methyl)trichlorosilane, ((2,3,5-tribromo-(4-methyl)phenyl)methyl)trichlorosilane and ((2,3,5,6-tetrabromo-(4-methyl)phenyl)methyl)trichlorosilane as the trichlorosilanes having a phenylalkyl group in which a methyl group is combined with a bromine atom, and (11-(3-chloro-4-methoxyphenyl)undecyl)trichlorosilane as the trichlorosilanes having a phenylalkyl group in which a methoxy group is combined with a chlorine atom.

Capable of being given are (3-phenoxypropyl)trichlorosilane as the trichlorosilanes having a phenylalkyl group in which at least one —CH$_2$— contained in alkylene, which is not adjacent, is replaced by —O—, ((2-phenyl)ethenyl)trichlorosilane, (3-phenyl-2-propenoyl)trichlorosilane and (14-phenyl-13-tetradecenoyl)trichlorosilane as the trichlorosilanes having a linear phenylalkenyl group having 20 or less carbon atoms, and ((1-phenyl)ethenyl)trichlorosilane and (4-phenyl-4-pentenoyl)trichlorosilane as the trichlorosilanes having a branched phenylalkenyl group having 20 or less carbon atoms.

Capable of being given are (2-(2,3,4,5,6-pentafluorophenyl)ethenyl)trichlorosilane as the trichlorosilanes having a phenylalkenyl group in which at least one hydrogen atom in a phenyl group is replaced by a fluorine atom, and (2-(4-methylphenyl)ethenyl)trichlorosilane as the trichlorosilanes having a phenylalkenyl group in which at least one hydrogen atom in a phenyl group is replaced by a methyl group. They are commercially available in the market or can be obtained by synthesizing by a publicly known method. Further, the trialkoxysilanes can readily be produced by substituting a hydrolyzable group of the trichlorosilanes.

In Formulas (1) and (2), further preferred R represents independently a linear, branched, or partially or wholly cyclic alkyl group having 8 or less carbon atoms (at least one hydrogen atom contained in the alkyl group may be replaced by a fluorine atom, and at least one —CH$_2$—, which is not adjacent, may be replaced by —O—), a linear alkenyl group having 9 or less carbon atoms, a partially or wholly cyclic alkenyl group having 9 or less carbon atoms, a phenyl group (at least one hydrogen atom contained in the phenyl group may be replaced by a fluorine atom, a chlorine atom, a bromine atom, a methyl group or a methoxy group), a non-substituted naphthalenyl group, or a linear or branched phenylalkyl group having 10 or less carbon atoms.

At least one hydrogen atom in a phenyl group contained in the phenylalkyl group may be replaced by a fluorine atom, a linear or branched alkyl group having 4 or less carbon atoms, an ethenyl group or a methoxy group. One —CH$_2$— in alkylene contained in the phenylalkyl group may be replaced by —O—. These selected R's may be the same or different, and are preferably the same.

Capable of being given as the specific examples of such R are methyl, ethyl, n-propyl, n-butyl, n-pentyl, n-hexyl, n-heptyl and n-octyl as the linear alkyl group having 8 or less carbon atoms, 1-methylethyl, 2-methylpropyl, 1,1-dimethylethyl, 1,1,2-trimethylpropyl and 2,4,4-trimethylpentyl as the branched alkyl group having 8 or less carbon atoms, and cyclohexylmethyl, cyclopentyl, cyclohexyl, 2-bicycloheptyl and cyclooctyl as the partially or wholly cyclic alkyl group having 8 or less carbon atoms.

Capable of being given are 3,3,3-trifluoropropyl, 3,3,4,4,5,5,6,6,6-nonadecafluorohexyl and tridecafluoro-1,1,2,2-tetrahydrooctyl as the alkyl group in which at least one hydrogen atom is replaced by a fluorine atom, 3-methoxypropyl and 3-heptafluoroisopropoxypropyl as the alkyl group in which at least one —CH$_2$—, which is not adjacent, is replaced by —O—, ethenyl, 2-propenyl, 3-butenyl, 5-hexenyl and 7-octenyl as the linear alkenyl group having 9 or less carbon atoms, and 2-(3-cyclohexenyl)ethyl, 5-(bicycloheptenyl)ethyl, 2-cyclopentenyl, 3-cyclohexenyl, 5-norbornene-2-yl and 4-cyclooctenyl as the partially or wholly cyclic alkenyl group having 9 or less carbon atoms.

Capable of being given are phenyl, pentafluorophenyl, 4-chlorophenyl and 4-bromophenyl as the phenyl group in which at least one hydrogen atom is replaced by a fluorine atom, a chlorine atom or a bromine atom, 4-methylphenyl as the phenyl group in which at least one hydrogen atom is replaced by a methyl group, and 4-methoxyphenyl as the phenyl group in which at least one hydrogen atom is replaced by a methoxy group.

Capable of being given are 1-naphthalenyl, phenylmethyl, 2-phenylethyl and 4-phenylbutyl as the linear phenylalkyl group having 10 or less carbon atoms, 2-phenylpropyl and 1-methyl-2-phenylethyl as the branched phenylalkyl group having 10 or less carbon atoms, and 3-(2,3,4,5,6-pentafluorophenyl)propyl as the phenylalkyl group in which at least one hydrogen atom in a phenyl group is replaced by a fluorine atom.

Capable of being given are 2-(4-ethylphenyl)ethyl, 2-(3-ethylphenyl)ethyl and 2-(4-(1,1-dimethylethyl)phenyl)ethyl as the phenylalkyl group in which at least one hydrogen atom in a phenyl group is replaced by a linear or branched alkyl group having 4 or less carbon atoms, and (2-(4-ethenyl)phenyl)ethyl and (1-(4-ethenyl)phenyl)ethyl as the phenylalkyl group in which at least one hydrogen atom in a phenyl group is replaced by an ethenyl group.

Capable of being given are 3-(4-methoxyphenyl)propyl as the phenylalkyl group in which at least one hydrogen atom in a phenyl group is replaced by a methoxy group, and 3-phenoxypropyl as the phenylalkyl group in which at least one —CH$_2$— in alkylene is replaced by —O—.

These selected R's may be the same or different, and are preferably the same.

Capable of being given as the specific examples of the trichlorosilanes and the trialkoxysilanes, which are the silane compounds having R described above and three hydrolyzable groups, are methyltrichlorosilane, ethyltrichlorosilane, n-propyltrichlorosilane, n-butyltrichlorosilane, n-pentyltrichlorosilane, n-hexyltrichlorosilane, n-heptyltrichlorosilane and n-octyltrichlorosilane as the trichlorosilanes having a linear alkyl group having 8 or less carbon atoms, and methyl-trimethoxysilane, methyltriethoxysilane, methyl-tripropoxysilane, ethyltrimethoxysilane, ethyl-triethoxysilane, n-propyltrimethoxysilane, n-propyl-triethoxysilane, n-butyltrimethoxysilane, n-pentyl-triethoxysilane, n-hexyltrimethoxysilane, n-hexyl-triethoxysilane, n-octyltrimethoxysilane and n-octyl-triethoxysilane as the trialkoxysilanes having a linear alkyl group having 8 or less carbon atoms.

Capable of being given are 1-methylethyltrichlorosilane, 2-methylpropyltrichlorosilane, 1,1-dimethylethyltrichlorosilane, 1,1,2-trimethylpropyltrichlorosilane and 2,4,4-trimethylpentyltrichlorosilane as the trichlorosilanes having a branched alkyl group having 8 or less carbon atoms, and 2-methylpropyltrimethoxysilane and 2,4,4-trimethylpentyltrimethoxysilane as the trialkoxysilanes having a branched alkyl group having 8 or less carbon atoms.

Capable of being given are cyclohexylmethyltrichlorosilane, cyclopentyltrichlorosilane, cyclohexyltrichlorosilane, 2-bicycloheptyltrichlorosilane and cyclooctyltrichlorosilane as the trichlorosilanes having a partially or wholly cyclic alkyl group having 8 or less carbon atoms, cyclopentyltrimethoxysilane and cyclohexyltrimethoxysilane as the trialkoxysilanes having a wholly cyclic alkyl group having 8 or less carbon atoms, and (3,3,3-trifluoropropyl)trichlorosilane, (3,3,4,4,5,5,6,6-nonadecafluorohexyl)trichlorosilane and (tridecafluoro-1,1,2,2-tetrahydrooctyl)trichlorosilane as the trichlorosilanes having an alkyl group in which at least one hydrogen atom is replaced by a fluorine atom.

Capable of being given are (3-heptafluoroisopropoxypropyl)trichlorosilane as the trichlorosilanes having an alkyl group in which at least one —$CH_2$— is replaced by —O—, 3-methoxypropyltrimethoxysilane as the trialkoxysilanes having an alkyl group in which at least one —$CH_2$— is replaced by —O—, and ethenyltrichlorosilane, 2-propenyltrichlorosilane, 5-hexenyltrichlorosilane and 7-octenyltrichlorosilane as the trichlorosilanes having a linear alkenyl group having 9 or less carbon atoms.

Capable of being given are ethenyltrimethoxysilane, ethenyltriethoxysilane, tris(1-methylethoxy)ethenylsilane, tris(1-methylpropoxy)ethenylsilane, tris(1,1-dimethylethoxy)ethenylsilane, 2-propenyltrimethoxysilane, 2-propenyltriethoxysilane, 3-butenyltriethoxysilane, 5-hexenyltrimethoxysilane and 7-octenyltrimethoxysilane as the trialkoxysilanes having a linear alkenyl group having 9 or less carbon atoms, and (2-(3-cyclohexenyl)ethyl)trichlorosilane, (5-(bicycloheptenyl)ethyl)trichlorosilane, 2-cyclopentenyltrichlorosilane, 3-cyclohexenyltrichlorosilane, trichloro(5-norbornene-2-yl)silane and 4-cyclooctenyltrichlorosilane as the trichlorosilanes having a partially or wholly cyclic alkyl group having 9 or less carbon atoms.

Capable of being given are triethoxy(5-norbornene-2-yl)silane as the trialkoxysilanes having a partially or wholly cyclic alkenyl group having 9 or less carbon atoms, phenyltrichlorosilane as the trichlorosilanes having a phenyl group, phenyltrimethoxysilane and phenyltriethoxysilane as the trialkoxysilanes having a phenyl group, pentafluorophenyltriethoxysilane as the trialkoxysilanes having a phenyl group in which at least one hydrogen atom is replaced by a fluorine atom, 4-chlorophenyltrichlorosilane as the trichlorosilanes having a phenyl group in which at least one hydrogen atom is replaced by a chlorine atom, and 4-chlorophenyltriethoxysilane as the trialkoxysilanes having a phenyl group in which at least one hydrogen atom is replaced by a chlorine atom.

Capable of being given are 4-bromophenyltrichlorosilane as the trichlorosilanes having a phenyl group in which at least one hydrogen atom is replaced by a bromine atom, 4-bromophenyltrimethoxysilane as the trialkoxysilanes having a phenyl group in which at least one hydrogen atom is replaced by a bromine atom, (4-methylphenyl)trichlorosilane as the trichlorosilanes having a phenyl group in which at least one hydrogen atom is replaced by a methyl group, and (4-methylphenyl)trimethoxysilane as the trialkoxysilanes having a phenyl group in which at least one hydrogen atom is replaced by a methyl group.

Capable of being given are ((4-methoxy)phenyl)trimethoxysilane as the trialkoxysilanes having a phenyl group in which at least one hydrogen atom is replaced by a methoxy group, (1-naphthalenyl)trimethoxysilane and (1-naphthalenyl)triethoxysilane as the trialkoxysilanes having a non-substituted naphthalenyl group, (phenylmethyl)trichlorosilane, (2-phenylethyl)trichlorosilane and (4-phenylbutyl)trichlorosilane as the trichlorosilanes having a linear phenylalkyl group having 10 or less carbon atoms, and (phenylmethyl)triethoxysilane and (2-phenylethyl)trimethoxysilane as the trialkoxysilanes having a linear phenylalkyl group having 10 or less carbon atoms.

Capable of being given are (2-phenylpropyl)trichlorosilane and (1-methyl-2-phenylethyl)trichlorosilane as the trichlorosilanes having a branched phenylalkyl group having 10 or less carbon atoms, (3-(2,3,4,5,6-pentafluorophenyl)propyl)trichlorosilane as the trichlorosilanes having a phenylalkyl group in which at least one hydrogen atom in a phenyl group is replaced by a fluorine atom, and (2-(4-ethylphenyl)ethyl)trimethoxysilane and (2-(3-ethylphenyl)ethyl)trimethoxysilane as the trialkoxysilanes having a phenylalkyl group in which at least one hydrogen atom in a phenyl group is replaced by a linear alkyl group having 4 or less carbon atoms.

Capable of being given are (2-(4-(1,1-dimethylethyl)phenyl)ethyl)trichlorosilane as the trichlorosilanes having a phenylalkyl group in which at least one hydrogen atom in a phenyl group is replaced by a branched alkyl group having 4 or less carbon atoms, ((2-(4-ethenyl)phenyl)ethyl)trimethoxysilane and ((1-(4-ethenyl)phenyl)ethyl)trimethoxysilane as the trialkoxysilanes having a phenylalkyl group in which at least one hydrogen atom in a phenyl group is replaced by an ethenyl group, and (3-(4-methoxyphenyl)propyl)trichlorosilane as the trichlorosilanes having a phenylalkyl group in which at least one hydrogen atom in a phenyl group is replaced by a methoxy group.

Capable of being given are (3-phenoxypropyl)trichlorosilane as the trichlorosilanes having a phenylalkyl group in which at least one —$CH_2$— in alkylene is replaced by —O—.

They are commercially available in the market and can readily be obtained. The trialkoxysilanes can easily be produced by substituting a hydrolyzable group of the trichlorosilanes.

In Formulas (1) and (2), most preferred R is a phenyl group (at least one hydrogen atom contained in the phenyl group may be replaced by a fluorine atom, a chlorine atom, a bromine atom, a methyl group or a methoxy group), a non-substituted naphthalenyl group, or a linear or branched phenylalkyl group having 10 or less carbon atoms (at least one hydrogen atom in a phenyl group contained in the phenylalkyl group may be replaced by a fluorine atom, a linear or branched alkyl group having 4 or less carbon atoms, an ethenyl group or a methoxy group, and one —$CH_2$— in alkylene contained in this phenylalkyl group may be replaced by —O—).

And, these selected R's are preferably the same.

Capable of being given as the specific examples of such R are a phenyl, pentafluorophenyl, 4-chlorophenyl and 4-bromophenyl as the phenyl group in which at least one hydrogen atom is replaced by a fluorine atom, a chlorine atom or a bromine atom, 4-methylphenyl as the phenyl group in which at least one hydrogen atom is replaced by a methyl group, (4-methoxy)phenyl as the phenyl group in which at least one hydrogen atom is replaced by a methoxy group, 1-naphthalenyl, and phenylmethyl, 2-phenylethyl and 4-phenylbutyl as the linear phenylalkyl group having 10 or less carbon atoms.

Capable of being given are 2-phenylpropyl and 1-methyl-2-phenylethyl as the branched phenylalkyl group having 10 or less carbon atoms, (3-(2,3,4,5,6-pentafluorophenyl)propyl as the phenylalkyl group in which at least one hydrogen atom in a phenyl group is replaced by a fluorine atom, (2-(4-ethylphenyl)ethyl and (2-(3-ethylphenyl)ethyl as the phenylalkyl group in which at least one hydrogen atom in a phenyl group is replaced by a linear alkyl group having 4 or less carbon atoms, 2-(4-(1,1-dimethylethyl)phenyl)ethyl as the phenylalkyl group in which at least one hydrogen atom in a phenyl group is replaced by a branched alkyl group having 4 or less carbon atoms, and (2-(4-ethenyl)phenyl) ethyl and (1-(4-ethenyl)phenyl)ethyl as the phenylalkyl group in which at least one hydrogen atom in a phenyl group is replaced by an ethenyl group.

Capable of being given are 3-(4-methoxyphenyl)propyl as the phenylalkyl group in which at least one hydrogen atom in a phenyl group is replaced by a methoxy group, and 3-phenoxypropyl as the phenylalkyl group in which at least one —CH$_2$— in alkylene is replaced by —O—.

And, these selected R's are preferably the same.

Capable of being given as the specific examples of the trichlorosilanes and the trialkoxysilanes, which are the silane compounds having R described above and three hydrolyzable groups, are phenyltrichlorosilane as the trichlorosilanes having a phenyl group, phenyltrimethoxysilane and phenyltriethoxysilane as the trialkoxysilanes having a phenyl group, pentafluorophenyltriethoxysilane as the trialkoxysilanes having a phenyl group in which at least one hydrogen atom is replaced by a fluorine atom, 4-chlorophenyltrichlorosilane as the trichlorosilanes having a phenyl group in which at least one hydrogen atom is replaced by a chlorine atom, 4-chlorophenyltriethoxysilane as the trialkoxysilanes having a phenyl group in which at least one hydrogen atom is replaced by a chlorine atom, 4-bromophenyltrichlorosilane as the trichlorosilanes having a phenyl group in which at least one hydrogen atom is replaced by a bromine atom, 4-bromophenyltrimethoxysilane as the trialkoxysilanes having a phenyl group in which at least one hydrogen atom is replaced by a bromine atom, (4-methylphenyl)trichlorosilane as the trichlorosilanes having a phenyl group in which at least one hydrogen atom is replaced by a methyl group, (4-methylphenyl)trimethoxysilane as the trialkoxysilanes having a phenyl group in which at least one hydrogen atom is replaced by a methyl group, and ((4-methoxy)phenyl)trimethoxysilane as the trialkoxysilanes having a phenyl group in which at least one hydrogen atom is replaced by a methoxy group.

Capable of being given are (1-naphthalenyl)trimethoxysilane and (1-naphthalenyl)triethoxysilane as the trialkoxysilanes having a non-substituted naphthalenyl group, (phenylmethyl)trichlorosilane, (2-phenylethyl)trichlorosilane and (4-phenylbutyl)trichlorosilane as the trichlorosilanes having a linear phenylalkyl group having 10 or less carbon atoms, (phenylmethyl)triethoxysilane and (2-phenylethyl)trimethoxysilane as the trialkoxysilanes having a linear phenylalkyl group having 10 or less carbon atoms, (2-phenylpropyl)trichlorosilane and (1-methyl-2-phenylethyl)trichlorosilane as the trichlorosilanes having a branched phenylalkyl group having 10 or less carbon atoms, (3-(2,3,4,5,6-pentafluorophenyl)propyl)trichlorosilane as the trichlorosilanes having a phenylalkyl group in which at least one hydrogen atom in a phenyl group is replaced by a fluorine atom, and (2-(4-ethylphenyl)ethyl)trimethoxysilane and (2-(3-ethylphenyl)ethyl)trimethoxysilane as the trialkoxysilanes having a phenylalkyl group in which at least one hydrogen atom in a phenyl group is replaced by a linear alkyl group having 4 or less carbon atoms.

Capable of being given are (2-(4-(1,1-dimethylethyl)phenyl)ethyl)trichlorosilane as the trichlorosilanes having a phenylalkyl group in which at least one hydrogen atom in a phenyl group is replaced by a branched alkyl group having 4 or less carbon atoms, ((2-(4-ethenyl)phenyl)ethyl)trimethoxysilane and ((1-(4-ethenyl)phenyl)ethyl)trimethoxysilane as the trialkoxysilanes having a phenylalkyl group in which at least one hydrogen atom in a phenyl group is replaced by an ethenyl group, (3-(4-methoxyphenyl)propyl) trichlorosilane as the trichlorosilanes having a phenylalkyl group in which at least one hydrogen atom in a phenyl group is replaced by a methoxy group, and (3-phenoxypropyl) trichlorosilane as the trichlorosilanes having a phenylalkyl group in which at least one —CH$_2$— in alkylene is replaced by —O—.

They are commercially available in the market and can readily be obtained. The trialkoxysilanes can easily be produced by substituting a hydrolyzable group of the trichlorosilanes.

When polysilsesquioxane obtained by hydrolyzing the foregoing silane compound having three hydrolyzable groups is used to synthesize the organic silicon compound of the present invention, the polysilsesquioxane is obtained by hydrolyzing by a conventionally known method, and the hydrolyzing method shall not specifically be restricted.

M described above shall not specifically be restricted as long as it is alkaline metals, and for example, lithium, sodium, potassium and cesium are given as such alkaline metal.

Also, the hydroxides of the alkaline metals represented by M described above can be used for the monovalent alkaline metal hydroxide. To be specific, they include lithium hydroxide, sodium hydroxide, potassium hydroxide and cesium hydroxide, and commercially available products can be used for them as they are.

A use amount of the hydroxides of the alkaline metals is preferably 0.1 to 5 time mole, more preferably 0.2 to 1 time mole based on the silane compound having three hydrolyzable groups and represented by Formula (2). If it is larger than 5 time mole, cyclic, branched and linear siloxane compounds having a low molecular weight are liable to be produced. On the other hand, it is smaller than 0.1 time mole, high molecular weight products are liable to be produced, and a lot of compounds, which are not regulated in a structure, are likely to be produced.

An amount of water, which is used when synthesizing the organic silicon compound of the present invention by subjecting the silane compound having three hydrolyzable groups described above to hydrolysis and polycondensation in the presence of the monovalent alkaline metal hydroxide and the organic solvent, is preferably 0.5 to 5 time mole, more preferably 1 to 3 time mole based on the silane compound having three hydrolyzable groups. If the above amount of water is larger than 5 time mole, high molecular weight products are liable to be produced. On the other hand, if it is smaller than 0.5 time mole, hydrolysis does not sufficiently proceed, and siloxane compounds having a low molecular weight are liable to be produced or the hydrolyzable group is likely to remain.

Commercially available organic solvents can be used as the organic solvent described above, and among them, ethers or alcohols are preferred. In this case, dimethyl ether, diethyl ether, diisopropyl ether, tetrahydrofuran and 1,4-dioxane can be given as the ethers. Also, linear, branched or cyclic monohydric alcohols can be given as the alcohols. Capable of being given are, for example, methanol, ethanol, 1-propanol, 1-butanol, 1-hexanol and 1-octanol as the linear alcohols, 2-propanol, 2-butanol, 2-methyl-2-propanol, 2-hexanol and 3-hexanol as the branched alcohols, and cyclopentanol, cyclohexanol and cycloheptanol as the cyclic alcohols. But the above alcohols shall not be restricted to these alcohols given as the examples.

Time required until the reaction is finished is varied depending on conditions such as the kind and the amount of the organic solvent, and the reaction can be finished normally in several minutes to several hours. The reaction conditions are maintained, if necessary, for further 5 to 10 hours in a certain case in order to sufficiently complete the reaction. After finishing the reaction, the compound of the present invention can be separated by removing the solvent by filtration.

The organic silicon compound thus obtained can be analyzed as it is in order to confirm that it has the structure represented by Formula (1) described above, but because of reactivity given to the above organic silicon compound, the reaction is likely to take place in the middle of the analysis to obtain erroneous analytical results. In order to avoid it, the alkaline metal coordinated is replaced by a trimethylsilyl group to convert the above compound to an organic silicon compound represented by the following Formula (4) to suppress a progress in the reaction, whereby reliability of the analytical results can be raised. Further, the solubility in almost all organic solvents is elevated by converting to the organic silicon compound represented by Formula (4), so that the analytical method of the structure is diversified and facilitated.

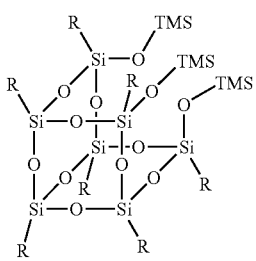

(4)

R in Formula (4) is the same as R in Formula (1) described above, and TMS represents a trimethylsilyl group.

When using, for example, polysilsesquioxane obtained by hydrolyzing the silane compound having three hydrolyzable groups in which R is a phenyl group, it was confirmed from proton nuclear magnetic resonance ($^1$H-NMR) and carbon-13 nuclear magnetic resonance ($^{13}$C-NMR) of the product that a phenyl group and a trimethylsilyl group were present in an integral ratio of 7:3, and confirmed from silicon-29 nuclear magnetic resonance ($^{29}$Si-NMR) that 11.547 ppm originating in the trimethylsilyl group and three kinds of peaks of −77.574 ppm, −78.137 ppm and −78.424 ppm (all based on tetramethylsilane), originating in the T structure having a phenyl group, were present in a ratio of 1:3:3, and it was indicated that the product had a structure represented by the following Formula (5). Further, it was confirmed from the measuring results obtained by mass spectrometry that the absolute molecular weight was consistent with the theoretical molecular weight of the structure represented by the following Formula (5). Further, confirmed from the analytical results obtained by an infrared absorption spectrum method (IR) were absorptions assigned respectively to deformation vibration of Si-Ph in 1430 and 1590 cm$^{-1}$, harmonic vibration of a substituted benzene ring in 1960 to 1760 cm$^{-1}$, stretching vibration of Si—O—Si in 1200 to 950 cm$^{-1}$ and vibration of Si—CH$_3$ in 1250 cm$^{-1}$. It is supported by these results that the compound replaced by a trimethylsilyl group has the structure represented by the following Formula (5), and this indicates that the organic silicon compound obtained has a structure represented by the following Formula (6):

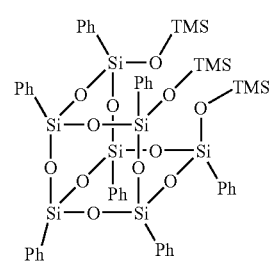

(5)

In Formula (5), Ph represents a phenyl group, and TMS represents a trimethylsilyl group.

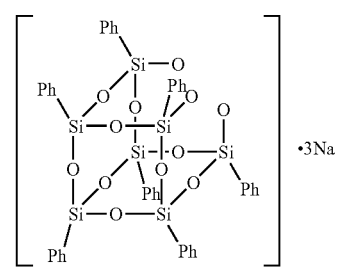

(6)

In Formula (6), Ph represents a phenyl group, and Na represents sodium.

The organic silicon compound of the present invention is a novel organic silicon compound from which various useful organic silicon compounds can be derived, and it is expected to be applied in a wide area. It is useful, for example, as an organic silicon compound which can be applied to wide fields such as a modifying agent for thermoplastic resins, an interlayer dielectric, a sealing material, a coating material and a flame retardant or as a raw material compound for them.

EXAMPLES

The present invention shall more specifically be explained with reference to examples, but the present invention shall by no means be restricted to these examples.

Example 1

(1) Synthesis of Polysilsesquioxane

A four neck separable flask having a content volume of 2 liter equipped with a reflux condenser, a thermometer and a dropping funnel was charged with 640.7 g of ice and water and 200 g of toluene and stirred by means of stirring blades to cool the inside of the flask to 0° C. Then, a mixed solution of 211.5 g of phenyltrichiorosilane and 130 g of toluene, dried on molecular sieves for a whole day and night, was dropwise added thereto at a temperature of not exceeding 2°

C. in one hour. Next, after stirring at a room temperature for 30 minutes, the solution was washed with refined water, and the solvent was distilled off by heating under reduced pressure to obtain 120.7 g of a residue. The residue thus obtained was analyzed by a gel permeation chromatography method (GPC method) to find that it was a solid matter having a weight average molecular weight of about 3,100 (not corrected) in terms of polystyrene.

(2) Synthesis of Organic Silicon Compound

A four neck flask having a content volume of 500 ml equipped with a reflux condenser and a thermometer was charged with 12.9 g of the polysilsesquioxane obtained above, 250 ml of tetrahydrofuran, dried on molecular sieves for a whole day and night, and 4.0 g of sodium hydroxide, and a rotator was put thereinto to heat and reflux the solution at 67° C. After about 4 hours, the solution started to get cloudy by deposition of fine powder, and refluxing was continued for one hour as it was to finish the reaction. A solid matter deposited was washed with tetrahydrofuran, filtered and dried under vacuum to obtain 10.1 g of a powdery solid matter.

Example 2

<Synthesis of Organic Silicon Compound>

A four neck flask having a content volume of one liter equipped with a reflux condenser, a thermometer and a dropping funnel was charged with 99 g of phenyltrimethoxysilane, 10 g of sodium hydroxide and 500 ml of 2-propanol, and a rotator put thereinto. Deionized water 11 g was dropwise added thereto from the dropping funnel in about 2 minutes while stirring at a room temperature by means of a magnetic stirrer, and then the flask was heated on an oil bath up to a temperature at which 2-propanol was refluxed. After refluxing was started, stirring was continued for 1.5 hour to complete the reaction. Then, the flask was pulled up from the oil bath and left standing still a night at a room temperature to completely deposit a solid matter produced. The solid matter deposited was filtrated through a pressure filter equipped with a membrane filter having a pore diameter of 0.1 μm. Then, the solid matter thus obtained was washed once with 2-propanol and dried at 70° C. for 4 hours in a vacuum dryer to obtain 66 g of a white powder solid matter.

Example 3

<Synthesis of Organic Silicon Compound>

A four neck flask having a content volume of 500 ml equipped with a reflux condenser, a thermometer and a dropping funnel was used to carry out reaction according to Example 2 to obtain 13 g of a white powder solid matter, except that used were 28 g of phenyltrimethoxysilane, 2.4 g of sodium hydroxide, 3.4 g of deionized water and 350 ml of tetrahydrofuran as an oxygen-containing organic solvent.

Example 4

<Introduction of Trimethylsilyl Group>

A four neck flask having a content volume of 200 ml equipped with a reflux condenser was charged with 2.0 g of the powdery solid matter obtained in Example 1, 100 g of toluene, 1.7 g of triethylamine, 1.4 g of trimethylchlorosilane and a rotator, and the mixture was stirred at a room temperature for 2 hours. After finishing the reaction, it was washed with refined water and dried under vacuum to obtain 2.1 g of a powdery solid matter.

The powdery solid matter thus obtained was subjected to structural analysis by means of $^1$H-NMR, $^{13}$C-NMR, $^{29}$Si-NMR, mass spectrometry and IR analysis. The results thereof are shown in FIG. 1 to FIG. 5. It was confirmed from a $^1$H-NMR chart shown in FIG. 1 and a $^{13}$C-NMR chart shown in FIG. 2 that a phenyl group and a trimethylsilyl group were present in an integral ratio of 7:3. It was confirmed from $^{29}$Si-NMR shown in FIG. 3 that 11.547 ppm originating in the trimethylsilyl group and three kinds of peaks of −77.574 ppm, −78.137 ppm and −78.424 originating in the T structure having a phenyl group (all based on tetramethylsilane) were present in a ratio of 1:3:3. It was confirmed from the measuring results of a mass spectrometric spectrum shown in FIG. 4 that the absolute molecular weight was consistent with the theoretical molecular weight of the structure represented by Formula (5) described above. Confirmed from the measuring results of an infrared absorption spectrum shown in FIG. 5 were absorptions assigned respectively to deformation vibration of Si—Ph in 1430 and 1590 cm$^{-1}$, harmonic vibration of a substituted benzene ring in 1960 to 1760 cm$^{-1}$, stretching vibration of Si—O—Si in 1200 to 950 cm$^{-1}$ and vibration of Si—CH$_3$ in 1250 cm$^{-1}$. These results support that the compound replaced by a trimethylsilyl group has the structure represented by Formula (5) described above, and this indicates that the organic silicon compound obtained has the structure represented by Formula (6) described above.

Example 5

<Introduction of Trichlorosilane>

A four neck flask having a content volume of 100 ml equipped with dropping funnel, a reflux condenser and a thermometer was charged with a rotator, 1.0 g of the powdery solid matter obtained in Example 1, 20 g of tetrahydrofuran and 0.121 g of triethylamine, and the flask was sealed with dry nitrogen. n-propyltrichlorosilane 0.213 g was dropwise added thereto from the dropping funnel while stirring by means of a magnetic stirrer. Subsequently, stirring was continued at a room temperature for one hour, and then the reaction was finished. Next, 20 g of deionized water was added thereto to hydrolyze unreacted n-propyltrichlorosilane. Then, the organic layer was washed by a normal method, dried on anhydrous magnesium sulfate, filtered and condensed under reduced pressure by means of a rotary evaporator to obtain a white solid matter. The white solid matter thus obtained was recrystallized from 30 ml of toluene to obtain 0.49 g of a powdery white solid matter. The yield calculated from the charged amount was 49%.

Figure 6:
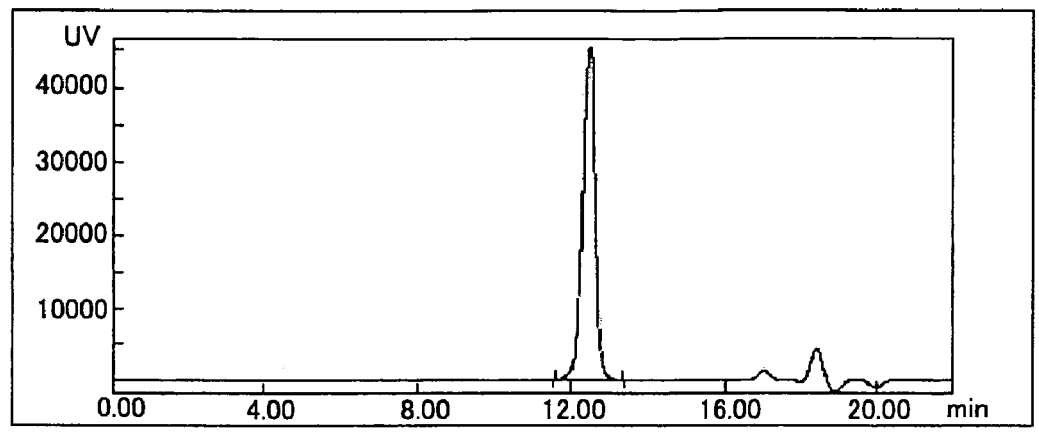
FIG. 6 is a GPC chart diagram of the organic silicon compound synthesized in Example 5.
Figure 6:
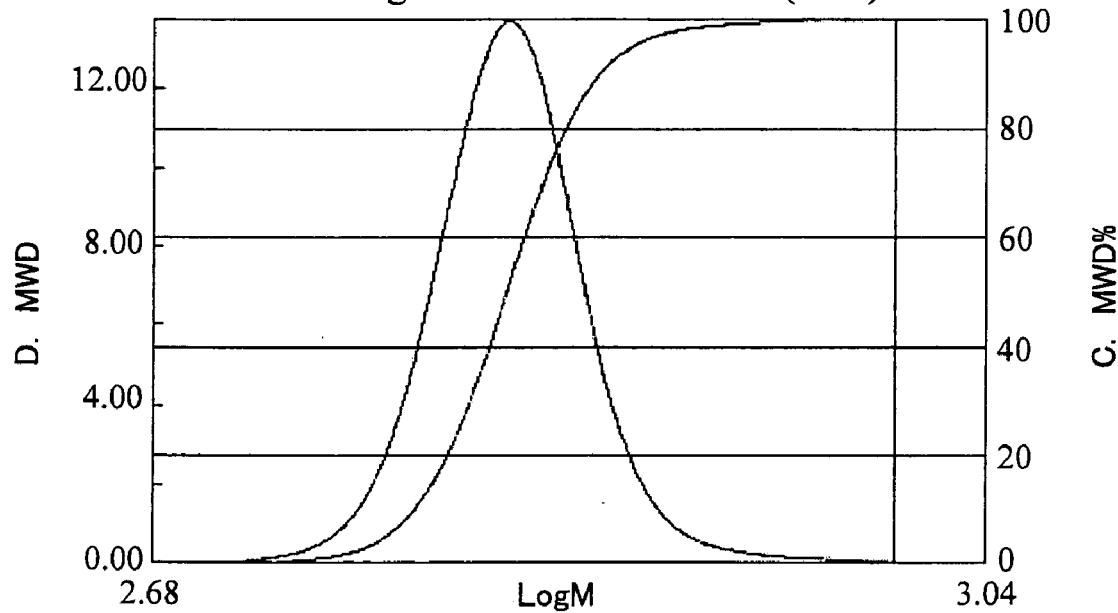
Figure 7:
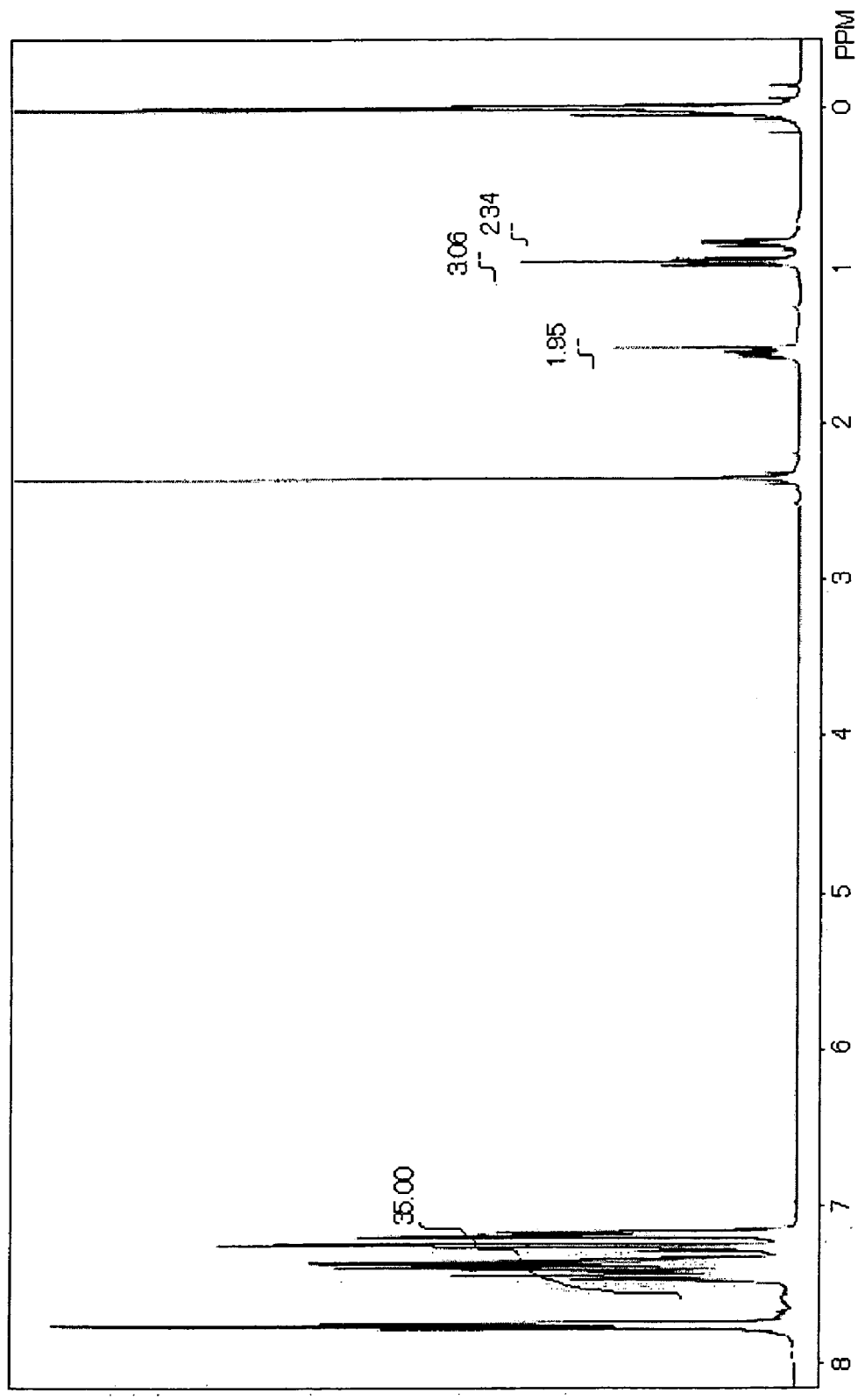
FIG. 7 is a $^1$H-NMR chart diagram of the organic silicon compound synthesized in Example 5.

The powdery white solid matter thus obtained was analyzed by means of a gel permeation chromatography method (GPC method) and $^1$H-NMR. The results thereof are shown in FIG. 6 and FIG. 7. It was confirmed from a GPC chart shown in FIG. 6 that the weight average molecular weight was 686 (non-corrected) in terms of polystyrene and that the purity was 99% or more. It was confirmed from a $^1$H-NMR chart shown in FIG. 7 that a phenyl group and an n-propyl group were present in a ratio of 7:1 and that the powdery white solid matter obtained had a structure shown by Formula (7):

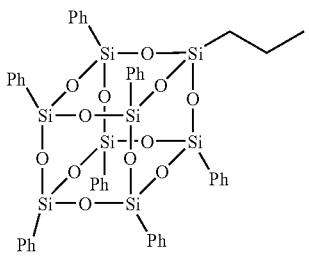

(7)

In Formula (7), Ph represents a phenyl group.

Comparative Example 1

<Introduction of Trichlorosilane>

Synthesis and analysis were carried out by the same methods as in Example 5, except that 0.93 g of a compound represented by the following Formula (8), which was obtained from Hybrid Plastics Co., Ltd., was used in stead of the compound of the present invention. However, since the reactive active group was a silanol group, the reactivity with n-propyltrichlorosilane was bad, and the targeted complete condensation product was not obtained, so that the powder was not recovered:

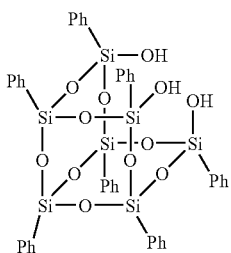

(8)

In Formula (8), Ph represents a phenyl group.

It was confirmed that use of the compound of the present invention made it possible to readily synthesize the complete condensation product at a good yield by reaction with trichlorosilanes. Further, the compound of the present invention has a high reactivity as well with trichlorosilanes. Compounds derived from it are not restricted to the complete condensation products.

INDUSTRIAL APPLICABILITY

The novel organic silicon compound of the present invention in which a structure is prescribed is a novel organic silicon compound which has a reactive active group and from which various useful organic silicon compounds can be derived making use of this reactive active group. Capable of being derived are, for example, various organic silicon compounds useful as a modifying agent for thermoplastic resins, an interlayer dielectric, a sealing material, a coating material and a flame retardant. The production process of the present invention is a production process in which the organic silicon compound described above can efficiently be produced.

What is claimed is:

1. An organic silicon compound represented by the following Formula (1):

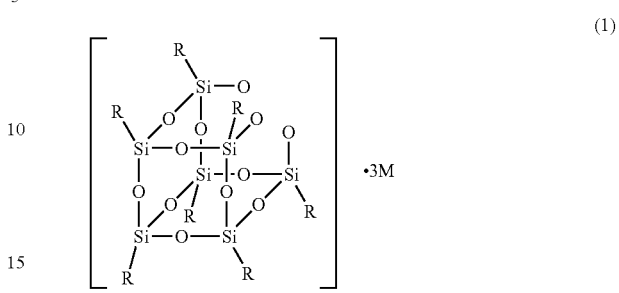

(1)

wherein R represents independently a hydrogen atom, a linear or branched alkyl group, a linear or branched alkenyl group, a partially or wholly cyclic alkenyl group, a substituted or non-substituted aryl group, a substituted or non-substituted arylalkyl group, or a substituted or non-substituted arylalkenyl group; in the alkyl group and alkenyl group, at least one hydrogen atom may be replaced by a fluorine atom, and at least one —$CH_2$—, which is not adjacent, may be replaced by —O—; in alkylene contained in the arylalkyl group, at least one hydrogen atom may be replaced by a fluorine atom, and at least one —$CH_2$—, which is not adjacent, may be replaced by —O—; in alkenylene contained in the arylalkenyl group, at least one hydrogen atom may be replaced by a fluorine atom, and at least one —$CH_2$—, which is not adjacent, may be replaced by —O—; R's in Formula (1) may be the same or different; and M represents a monovalent alkaline metal.

2. The organic silicon compound according to claim 1, wherein R in Formula (1) represents independently a hydrogen atom, a linear or branched alkyl group having 44 or less carbon atoms, a linear or branched alkenyl group having 45 or less carbon atoms, a partially or wholly cyclic alkenyl group having 45 or less carbon atoms, a substituted or non-substituted aryl group, a substituted or non-substituted arylalkyl group, or a substituted or non-substituted arylalkenyl group; in the alkyl group and alkenyl group, at least one hydrogen atom may be replaced by a fluorine atom, and at least one —$CH_2$—, which is not adjacent, may be replaced by —O—; in alkylene contained in the arylalkyl group, at least one hydrogen atom may be replaced by a fluorine atom, and at least one —$CH_2$—, which is not adjacent, may be replaced by —O—; in alkenylene contained in the arylalkenyl group, at least one hydrogen atom may be replaced by a fluorine atom, and at least one —$CH_2$—, which is not adjacent, may be replaced by —O—; and R's in Formula (1) may be the same or different.

3. The organic silicon compound according to claim 1, wherein R in Formula (1) represents independently a hydrogen atom, or a linear or branched alkyl group having 30 or less carbon atoms, at least one hydrogen atom contained in the alkyl group may be replaced by a fluorine atom, and at least one —$CH_2$—, which is not adjacent, contained in the alkyl group may be replaced by —O—; and R's in Formula (1) may be the same or different.

4. The organic silicon compound according to claim 1, wherein R in Formula (1) represents independently a linear alkenyl group having 22 or less carbon atoms, or a partially or wholly cyclic alkenyl group having 22 or less carbon atoms; at least one —$CH_2$—, which is not adjacent, contained in the alkenyl group may be replaced by —O—; and R's in Formula (1) may be the same or different.

5. The organic silicon compound according to claim 1, wherein R in Formula (1) represents independently a naphthalenyl group or a phenyl group; at least one hydrogen atom contained in the phenyl group may be replaced by a fluorine atom, a chlorine atom, a bromine atom, a linear or branched alkyl group having 10 or less carbon atoms, a linear or branched alkenyl group having 4 or less carbon atoms (at least one hydrogen atom contained in the alkenyl group may be replaced by a phenyl group), a linear or branched alkoxy group having 18 or less carbon atoms, a phenoxy group, a phenyl group or a phenylmethyl group, and the substituents on the phenyl group may be the same or different, but when different, they may be any combination of a methyl group and a fluorine atom, a methyl group and a chlorine atom, a methyl group and a bromine atom, an ethenyl group and a fluorine atom, an alkoxy group and a fluorine atom, an alkoxy group and a chlorine atom, and an alkoxy group and a bromine atom; and R's in Formula (1) may be the same or different.

6. The organic silicon compound according to claim 1, wherein R in Formula (1) represents independently a linear or branched phenylalkyl group having 17 or less carbon atoms, or a partially or wholly cyclic phenylalkyl group having 17 or less carbon atoms; at least one hydrogen atom in a phenyl group contained in the phenylalkyl group may be replaced by a fluorine atom, a chlorine atom, a bromine atom, a linear, branched, or partially or wholly cyclic alkyl group having 12 or less carbon atoms (at least one hydrogen atom contained in the alkyl group may be replaced by a fluorine atom), a linear alkenyl group having 3 or less carbon atoms, a linear alkoxy group having 10 or less carbon atoms (at least one hydrogen atom contained in the alkoxy group may be replaced by a fluorine atom), a methoxymethyl group, a phenoxy group or a phenyl group, and the substituents selected may be the same or different, but when different, they may be any combination of a methyl group and a methoxy group, a methyl group and a chlorine atom, a methyl group and a bromine atom, and a methoxy group and a chlorine atom; at least one —CH$_2$—, which is not adjacent, in alkylene contained in the phenylalkyl group may be replaced by —O—; and R's in Formula (1) may be the same or different.

7. The organic silicon compound according to claim 1, wherein R in Formula (1) represents independently a linear or branched phenylalkenyl group having 20 or less carbon atoms; at least one hydrogen atom in a phenyl group contained in the phenylalkenyl group may be replaced by a fluorine atom or a methyl group; and R's in Formula (1) may be the same or different.

8. The organic silicon compound according to claim 1, wherein R in Formula (1) represents independently a linear or branched alkyl group having 8 or less carbon atoms (in the alkyl group, at least one hydrogen atom may be replaced by a fluorine atom, and at least one —CH$_2$—, which is not adjacent, may be replaced by —O—), a linear alkenyl group having 9 or less carbon atoms, a partially or wholly cyclic alkenyl group having 9 or less carbon atoms, a phenyl group, a non-substituted naphthalenyl group, or a linear or branched phenylalkyl group having 10 or less carbon atoms; at least one hydrogen atom contained in the phenyl group may be replaced by a fluorine atom, a chlorine atom, a bromine atom, a methyl group or a methoxy group; at least one hydrogen atom in a phenyl group contained in the phenylalkyl group may be replaced by a fluorine atom, a linear or branched alkyl group having 4 or less carbon atoms, an ethenyl group or a methoxy group; one —CH$_2$— in alkylene contained in the phenylalkyl group may be replaced by —O—; and R's in Formula (1) may be the same or different.

9. The organic silicon compound according to claim 1, wherein R in Formula (1) represents a linear or branched alkyl group having 8 or less carbon atoms (in the alkyl group, at least one hydrogen atom may be replaced by a fluorine atom, and at least one —CH$_2$—, which is not adjacent, may be replaced by —O—), a linear alkenyl group having 9 or less carbon atoms, a partially or wholly cyclic alkenyl group having 9 or less carbon atoms, a phenyl group, a non-substituted naphthalenyl group, or a linear or branched phenylalkyl group having 10 or less carbon atoms; at least one hydrogen atom contained in the phenyl group may be replaced by a fluorine atom, a chlorine atom, a bromine atom, a methyl group or a methoxy group; at least one hydrogen atom in a phenyl group contained in the phenylalkyl group may be replaced by a fluorine atom, a linear or branched alkyl group having 4 or less carbon atoms, an ethenyl group or a methoxy group; one —CH$_2$— in alkylene contained in the phenylalkyl group may be replaced by —O—; and R's in Formula (1) are the same group.

10. The organic silicon compound according to claim 1, wherein R in Formula (1) represents a phenyl group (at least one hydrogen atom contained in the phenyl group may be replaced by a fluorine atom, a chlorine atom, a bromine atom, a methyl group or a methoxy group), a non-substituted naphthalenyl group, or a linear or branched phenylalkyl group having 10 or less carbon atoms; at least one hydrogen atom in a phenyl group contained in the phenylalkyl group may be replaced by a fluorine atom, a linear or branched alkyl group having 4 or less carbon atoms, an ethenyl group or a methoxy group; one —CH$_2$— in alkylene contained in the phenylalkyl group may be replaced by —O—; and R's in Formula (1) are the same group.

11. The organic silicon compound according to claim 1, wherein R in Formula (1) is a non-substituted phenyl group.

12. The organic silicon compound according to claim 1, wherein the monovalent alkaline metal represented by M is sodium.

13. A production process for the organic silicon compound represented by Formula (1), characterized by reacting polysilsesquioxane, which is obtained by hydrolyzing a silane compound having three hydrolyzable groups and represented by the following Formula (2), with a monovalent alkaline metal hydroxide in an organic solvent:

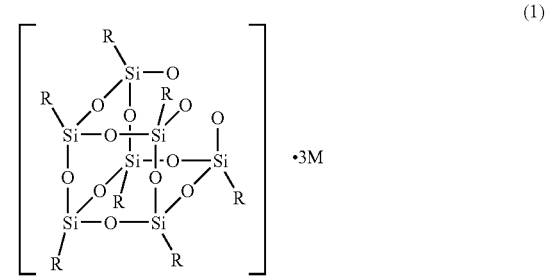

wherein R represents independently a hydrogen atom, a linear or branched alkyl group, a linear or branched alkenyl group, a partially or wholly cyclic alkenyl group, a substituted or non-substituted aryl group, a substituted or non-substituted arylalkyl group, or a substituted or non-substituted arylalkenyl group; in the alkyl group and alkenyl group, at least one hydrogen atom may be replaced by a fluorine atom, and at least one —CH$_2$—, which is not adjacent, may be replaced by —O—; in alkylene contained in the arylalkyl group, at least one hydrogen atom may be replaced by a fluorine atom, and at least one —CH$_2$—, which is not adjacent, may be replaced by —O—; in alkenylene contained in the arylalkenyl group, at least one hydrogen atom may be replaced by a fluorine atom, and at least one —CH$_2$—, which is not adjacent, may be replaced by —O—; R's in Formula (1) may be the same or different; and M represents a monovalent alkaline metal;

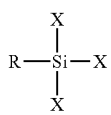

(2)

wherein R is defined in the same manner as R in Formula (1), and X represents a hydrolyzable group.

14. The production process for the organic silicon compound according to claim 13, wherein R in Formula (2) represents a hydrogen atom, a linear or branched alkyl group having 44 or less carbon atoms, a linear or branched alkenyl group having 45 or less carbon atoms, a partially or wholly cyclic alkenyl group having 45 or less carbon atoms, a substituted or non-substituted aryl group, a substituted or non-substituted arylalkyl group, or a substituted or non-substituted arylalkenyl group; in the alkyl group and alkenyl group, at least one hydrogen atom may be replaced by a fluorine atom, and at least one —CH$_2$—, which is not adjacent, may be replaced by —O—; in alkylene contained in the arylalkyl group, at least one hydrogen atom may be replaced by a fluorine atom, and at least one —CH$_2$—, which is not adjacent, may be replaced by —O—; in alkenylene contained in the arylalkenyl group, at least one hydrogen atom may be replaced by a fluorine atom, and at least one —CH$_2$—, which is not adjacent, may be replaced by —O—; and R's in Formula (1) may be the same or different.

15. The production process for the organic silicon compound according to claim 13, wherein R in Formula (2) represents a hydrogen atom, or a linear or branched alkyl group having 30 or less carbon atoms; at least one hydrogen atom contained in the alkyl group may be replaced by a fluorine atom, and at least one —CH$_2$—, which is not adjacent, contained in the alkyl group may be replaced by —O—; and R's in Formula (1) may be the same or different.

16. The production process for the organic silicon compound according to claim 13, wherein R in Formula (2) represents a linear alkenyl group having 22 or less carbon atoms, or a partially or wholly cyclic alkenyl group having 22 or less carbon atoms; at least one —CH$_2$—, which is not adjacent, contained in the alkenyl group may be replaced by —O—; and R's in Formula (1) may be the same or different.

17. The production process for the organic silicon compound according to claim 13, wherein R in Formula (2) represents independently a naphthalenyl group or a phenyl group; at least one hydrogen atom contained in the phenyl group may be replaced by a fluorine atom, a chlorine atom, a bromine atom, a linear or branched alkyl group having 10 or less carbon atoms, a linear or branched alkenyl group having 4 or less carbon atoms (at least one hydrogen atom contained in the alkenyl group may be replaced by a phenyl group), a linear or branched alkoxy group having 18 or less carbon atoms, a phenoxy group, a phenyl group or a phenylmethyl group, and the substituents selected may be the same or different, but when different, they may be any combination of a methyl group and a fluorine atom, a methyl group and a chlorine atom, a methyl group and a bromine atom, an ethenyl group and a fluorine atom, an alkoxy group and a fluorine atom, an alkoxy group and a chlorine atom, and an alkoxy group and a bromine atom; and R's in Formula (1) may be the same or different.

18. The production process for the organic silicon compound according to claim 13, wherein R in Formula (2) represents a linear or branched phenylalkyl group having 17 or less carbon atoms, or a partially or wholly cyclic phenylalkyl group having 17 or less carbon atoms; at least one hydrogen atom in a phenyl group contained in the phenylalkyl group may be replaced by a fluorine atom, a chlorine atom, a bromine atom, a linear, branched, or partially or wholly cyclic alkyl group having 12 or less carbon atoms (at least one hydrogen atom contained in the alkyl group may be replaced by a fluorine atom), a linear alkenyl group having 3 or less carbon atoms, a linear alkoxy group having 10 or less carbon atoms (at least one hydrogen atom contained in the alkoxy group may be replaced by a fluorine atom), a methoxymethyl group, a phenoxy group or a phenyl group, and the substituents selected may be the same or different, but when different, they may be any combination of a methyl group and a methoxy group, a methyl group and a chlorine atom, a methyl group and a bromine atom, and a methoxy group and a chlorine atom; at least one —CH$_2$—, which is not adjacent, in alkylene contained in the phenylalkyl group may be replaced by —O—; and R's in Formula (1) may be the same or different.

19. The production process for the organic silicon compound according to claim 13, wherein R in Formula (2) represents a linear or branched phenylalkenyl group having 20 or less carbon atoms; at least one hydrogen atom in a phenyl group contained in the phenylalkenyl group may be replaced by a fluorine atom or a methyl group; and R's in Formula (1) may be the same or different.

20. The production process for the organic silicon compound according to claim 13, wherein R in Formula (2) represents a linear or branched alkyl group having 8 or less carbon atoms (in the alkyl group, at least one hydrogen atom may be replaced by a fluorine atom, and at least one —CH$_2$—, which is not adjacent, may be replaced by —O—), a linear alkenyl group having 9 or less carbon atoms, a partially or wholly cyclic alkenyl group having 9 or less carbon atoms, a phenyl group, a non-substituted naphthalenyl group, or a linear or branched phenylalkyl group having 10 or less carbon atoms; at least one hydrogen atom contained in the phenyl group may be replaced by a fluorine atom, a chlorine atom, a bromine atom, a methyl group or a methoxy group; at least one hydrogen atom in a phenyl group contained in the phenylalkyl group may be replaced by a fluorine atom, a linear or branched alkyl group having 4 or less carbon atoms, an ethenyl group or a methoxy group; one —CH$_2$— in alkylene contained in the phenylalkyl group may be replaced by —O—; and R's in Formula (1) may be the same or different.

21. The production process for the organic silicon compound according to claim 13, wherein R in Formula (2) represents a linear or branched alkyl group having 8 or less carbon atoms (in the alkyl group, at least one hydrogen atom may be replaced by a fluorine atom, and at least one —CH$_2$—, which is not adjacent, may be replaced by —O—), a linear alkenyl group having 9 or less carbon atoms, a partially or wholly cyclic alkenyl group having 9 or less carbon atoms, a phenyl group, a non-substituted naphthalenyl group, or a linear or branched phenylalkyl group having 10 or less carbon atoms; at least one hydrogen atom contained in the phenyl group may be replaced by a fluorine atom, a chlorine atom, a bromine atom, a methyl group or a methoxy group; at least one hydrogen atom in a phenyl group contained in the phenylalkyl group may be replaced by a fluorine atom, a linear or branched alkyl group having 4 or less carbon atoms, an ethenyl group or a methoxy group; one —CH$_2$— in alkylene contained in the phenylalkyl group may be replaced by —O—; and R's in Formula (1) are the same group.

22. The production process for the organic silicon compound according to claim 13, wherein R in Formula (2) represents a phenyl group (at least one hydrogen atom contained in the phenyl group may be replaced by a fluorine atom, a chlorine atom, a bromine atom, a methyl group or a methoxy group), a non-substituted naphthalenyl group, or a linear or branched phenylalkyl group having 10 or less carbon atoms; at least one hydrogen atom in a phenyl group contained in the phenylalkyl group may be replaced by a fluorine atom, a linear or branched alkyl group having 4 or less carbon atoms, an ethenyl group or a methoxy group; one —CH$_2$— in alkylene contained in the phenylalkyl group may be replaced by —O—; and R's in Formula (1) are the same group.

23. The production process for the organic silicon compound according to claim 13, wherein R in Formula (2) is a non-substituted phenyl group.

24. A production process for the organic silicon compound represented by Formula (1), characterized by subjecting the silane compound, having three hydrolyzable groups and represented by Formula (2), to hydrolysis and polycondensation in the presence of an organic solvent and an alkaline metal hydroxide:

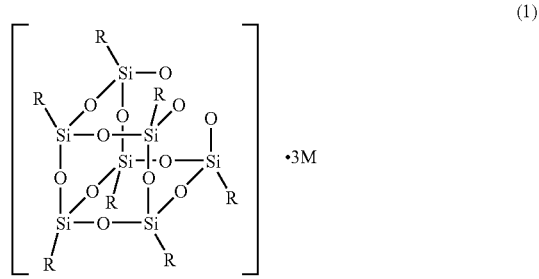

(1)

wherein R represents independently a hydrogen atom, a linear or branched alkyl group, a linear or branched alkenyl group, a partially or wholly cyclic alkenyl group, a substituted or non-substituted aryl group, a substituted or non-substituted arylalkyl group, or a substituted or non-substituted arylalkenyl group; in the alkyl group and alkenyl group, at least one hydrogen atom may be replaced by a fluorine atom, and at least one —CH$_2$—, which is not adjacent, may be replaced by —O—; in alkylene contained in the arylalkyl group, at least one hydrogen atom may be replaced by a fluorine atom, and at least one —CH$_2$—, which is not adjacent, may be replaced by —O—; in alkenylene contained in the arylalkenyl group, at least one hydrogen atom may be replaced by a fluorine atom, and at least one —CH$_2$—, which is not adjacent, may be replaced by —O—; R's in Formula (1) may be the same or different; and M represents a monovalent alkaline metal;

(2)

wherein R is defined in the same manner as R in Formula (1), and X represents a hydrolyzable group.

25. The production process for the organic silicon compound according to claim 24, wherein R in Formula (2) represents a hydrogen atom, a linear or branched alkyl group having 44 or less carbon atoms, a linear or branched alkenyl group having 45 or less carbon atoms, a partially or wholly cyclic alkenyl group having 45 or less carbon atoms, a substituted or non-substituted aryl group, a substituted or non-substituted arylalkyl group, or a substituted or non-substituted arylalkenyl group; in the alkyl group and alkenyl group, at least one hydrogen atom may be replaced by a fluorine atom, and at least one —CH$_2$—, which is not adjacent, may be replaced by —O—; in alkylene contained in the arylalkyl group, at least one hydrogen atom may be replaced by a fluorine atom, and at least one —CH$_2$—, which is not adjacent, may be replaced by —O—; in alkenylene contained in the arylalkenyl group, at least one hydrogen atom may be replaced by a fluorine atom, and at least one —CH$_2$—, which is not adjacent, may be replaced by —O—; and R's in Formula (1) may be the same or different.

26. The production process for the organic silicon compound according to claim 24, wherein R in Formula (2) represents a hydrogen atom, or a linear or branched alkyl group having 30 or less carbon atoms; at least one hydrogen atom contained in the alkyl group may be replaced by a fluorine atom, and at least one —CH$_2$—, which is not adjacent, contained in the alkyl group may be replaced by —O—; and R's in Formula (1) may be the same or different.

27. The production process for the organic silicon compound according to claim 24, wherein R in Formula (2) represents a linear alkenyl group having 22 or less carbon atoms, or a partially or wholly cyclic alkenyl group having 22 or less carbon atoms; at least one —CH$_2$—, which is not adjacent, contained in the alkenyl group may be replaced by —O—; and R's in Formula (1) may be the same or different.

28. The production process for the organic silicon compound according to claim 24, wherein R in Formula (2) represents independently a naphthalenyl group or a phenyl group; at least one hydrogen atom contained in the phenyl group may be replaced by a fluorine atom, a chlorine atom, a bromine atom, a linear or branched alkyl group having 10 or less carbon atoms, a linear or branched alkenyl group having 4 or less carbon atoms (at least one hydrogen atom contained in the alkenyl group may be replaced by a phenyl group), a linear or branched alkoxy group having 18 or less carbon atoms, a phenoxy group, a phenyl group or a phenylmethyl group, and the substituents selected may be the same or different, but when different, they may be any combination of a methyl group and a fluorine atom, a methyl group and a chlorine atom, a methyl group and a bromine atom, an ethenyl group and a fluorine atom, an alkoxy group and a fluorine atom, an alkoxy group and a chlorine atom, and an alkoxy group and a bromine atom; and R's in Formula (1) may be the same or different.

29. The production process for the organic silicon compound according to claim 24, wherein R in Formula (2) represents a linear or branched phenylalkyl group having 17 or less carbon atoms, or a partially or wholly cyclic phenylalkyl group having 17 or less carbon atoms; at least one hydrogen atom in a phenyl group contained in the phenylalkyl group may be replaced by a fluorine atom, a chlorine atom, a bromine atom, a linear, branched, or partially or wholly cyclic alkyl group having 12 or less carbon atoms (at least one hydrogen atom contained in the alkyl group may be replaced by a fluorine atom), a linear alkenyl group having 3 or less carbon atoms, a linear alkoxy group having 10 or less carbon atoms (at least one hydrogen atom contained in the alkoxy group may be replaced by a fluorine atom), a methoxymethyl group, a phenoxy group or a phenyl group, and the substituents selected may be the same or different, but when different, they may be any combination of a methyl group and a methoxy group, a methyl group and a chlorine atom, a methyl group and a bromine atom, and a methoxy group and a chlorine atom; at least one —CH$_2$—, which is not adjacent, in alkylene contained in the phenylalkyl group may be replaced by —O—; and R's in Formula (1) may be the same or different.

30. The production process for the organic silicon compound according to claim 24, wherein R in Formula (2) represents a linear or branched phenylalkenyl group having 20 or less carbon atoms; at least one hydrogen atom in a phenyl group contained in the phenylalkenyl group may be replaced by a fluorine atom or a methyl group; and R's in Formula (1) may be the same or different.

31. The production process for the organic silicon compound according to claim 24, wherein R in Formula (2) represents a linear or branched alkyl group having 8 or less carbon atoms (in the alkyl group, at least one hydrogen atom may be replaced by a fluorine atom, and at least one —CH$_2$—, which is not adjacent, may be replaced by —O—), a linear alkenyl group having 9 or less carbon atoms, a partially or wholly cyclic alkenyl group having 9 or less carbon atoms, a phenyl group, a non-substituted naphthalenyl group, or a linear or branched phenylalkyl group having 10 or less carbon atoms; at least one hydrogen atom contained in the phenyl group may be replaced by a fluorine atom, a chlorine atom, a bromine atom, a methyl group or a methoxy group; at least one hydrogen atom in a phenyl group contained in the phenylalkyl group may be replaced by a fluorine atom, a linear or branched alkyl group having 4 or less carbon atoms, an ethenyl group or a methoxy group; one —CH$_2$— in alkylene contained in the phenylalkyl group may be replaced by —O—; and R's in Formula (1) may be the same or different.

32. The production process for the organic silicon compound according to claim 24, wherein R in Formula (2) represents a linear or branched alkyl group having 8 or less carbon atoms (in the alkyl group, at least one hydrogen atom may be replaced by a fluorine atom, and at least one —CH$_2$—, which is not adjacent, may be replaced by —O—), a linear alkenyl group having 9 or less carbon atoms, a partially or wholly cyclic alkenyl group having 9 or less carbon atoms, a phenyl group, a non-substituted naphthalenyl group, or a linear or branched phenylalkyl group having 10 or less carbon atoms; at least one hydrogen atom contained in the phenyl group may be replaced by a fluorine atom, a chlorine atom, a bromine atom, a methyl group or a methoxy group; at least one hydrogen atom in a phenyl group contained in the phenylalkyl group may be replaced by a fluorine atom, a linear or branched alkyl group having 4 or less carbon atoms, an ethenyl group or a methoxy group; one —CH$_2$— in alkylene contained in the phenylalkyl group may be replaced by —O—; and R's in Formula (1) are the same group.

33. The production process for the organic silicon compound according to claim 24, wherein R in Formula (2) represents a phenyl group (at least one hydrogen atom contained in the phenyl group may be replaced by a fluorine atom, a chlorine atom, a bromine atom, a methyl group or a methoxy group), a non-substituted naphthalenyl group, or a linear or branched phenylalkyl group having 10 or less carbon atoms; at least one hydrogen atom in a phenyl group contained in the phenylalkyl group may be replaced by a fluorine atom, a linear or branched alkyl group having 4 or less carbon atoms, an ethenyl group or a methoxy group; one —CH$_2$— in alkylene contained in the phenylalkyl group may be replaced by —O—; and R's in Formula (1) are the same group.

34. The production process for the organic silicon compound according to claim 24, wherein R in Formula (2) is a non-substituted phenyl group.

35. The production process for the organic silicon compound according to claim 13, wherein metal of the monovalent alkaline metal oxide is sodium.

36. The production process for the organic silicon compound according to claim 24, wherein metal of the monovalent alkaline metal oxide is sodium.

37. The production process for the organic silicon compound according to claim 13, wherein the organic solvent is alcohol or ether.

38. The production process for the organic silicon compound according to claim 24, wherein the organic solvent is alcohol or ether.

* * * * *